(12) United States Patent
Kimoto et al.

(10) Patent No.: US 6,859,737 B2
(45) Date of Patent: Feb. 22, 2005

(54) GAS DETECTION APPARATUS AND AUTOMATIC VENTILATION SYSTEM FOR VEHICLE

(75) Inventors: Yuji Kimoto, Aichi (JP); Toshiya Matsuoka, Gifu (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 10/305,358

(22) Filed: Nov. 27, 2002

(65) Prior Publication Data

US 2003/0110828 A1 Jun. 19, 2003

(30) Foreign Application Priority Data

Nov. 29, 2001 (JP) ........................................ 2001-364211

(51) Int. Cl.$^7$ ............................................... G06F 19/00
(52) U.S. Cl. .......................................... 702/24; 73/1.02
(58) Field of Search .......................... 702/23, 24, 183, 702/184, 189; 73/1.02, 1.06, 19.01, 23.2, 23.21, 23.22, 23.4

(56) References Cited

U.S. PATENT DOCUMENTS

| | | | |
|---|---|---|---|
| 4,458,242 A | * | 7/1984 | Kusanagi et al. ........... 340/634 |
| 4,730,590 A | | 3/1988 | Sogawa ..................... 123/489 |
| 5,320,577 A | | 6/1994 | Tooru et al. |
| 5,426,937 A | | 6/1995 | Ohuchi et al. ................ 60/276 |
| 6,128,945 A | * | 10/2000 | Shioiri et al. .............. 73/31.06 |
| 6,172,759 B1 | * | 1/2001 | Goldstein ................... 356/437 |
| 6,370,940 B2 | * | 4/2002 | Warburton ................. 73/23.21 |

FOREIGN PATENT DOCUMENTS

| | | |
|---|---|---|
| JP | 1-199142 | 8/1989 |
| JP | 5-157714 | 6/1993 |
| JP | 11-42925 | 2/1999 |
| JP | 11-240323 | 9/1999 |

* cited by examiner

Primary Examiner—Edward Raymond
(74) Attorney, Agent, or Firm—Morgan, Lewis & Bockius LLP

(57) ABSTRACT

A gas detection apparatus incorporating a gas sensor element and a vehicle automatic ventilation system including the apparatus in which a sensor output value $S(n)$ is obtained, and a base value $B(n)$ is calculated by use of Expression (1): $B(n)=B(n-1)+k1[S(n)-B(n-1)]-k2[S(n)-S(n-5)]$ in the case where $S(n) \geq B(n-1)$, or by use of Expression (3): $B(n)=S(n)$ in the case where $S(n)<B(n-1)$, followed by calculation of a difference value $D(n)$; i.e., $S(n)-B(n)$. When the difference value exceeds a predetermined high connection threshold, a high-concentration signal is generated to close a flap. After that, the base value $B(n)$ is calculated by use of Expression (4): $B(n)=B(n-1)+k3[S(n)-B(n-1)]-k4[S(n)-S(n-5)]$. When the difference value becomes smaller than a predetermined low-concentration threshold, a low-concentration signal is generated to open the flap.

25 Claims, 8 Drawing Sheets

GAS DETECTION APPARATUS AND AUTOMATIC VENTILATION SYSTEM FOR VEHICLE

This application claims the benefit of the Japanese Patent Application No. 2001-364211 filed in Japan on Nov. 29, 2001, which is hereby incorporated by reference in its entirety.

BACKGROUND OF THE INVENTION

1. Field of the Invention

The present invention relates to a gas detection apparatus that detects a change in a concentration of a specific gas in an environment by use of a gas sensor element, and to an automatic ventilation system for a vehicle.

2. Prior Art

Conventionally, there has been known a gas sensor element which utilizes Ph-phthalocyanine or a metal oxide semiconductor such as $WO_3$ or $SnO_2$ and whose resistance changes with concentration of a specific gas, such as an oxidative gas (e.g., $NO_x$) or a reducing gas (e.g., CO, HC (hydrocarbon)) present in an environment. Further, there has been known a gas detection apparatus which utilizes such a gas sensor and detects change in concentration of a specific gas on the basis of change in the sensor resistance. Moreover, there have been known various types of control systems using such a gas detection apparatus; e.g., an automatic ventilation system for a vehicle in which a flap is opened and closed in accordance with the degree of contamination of air outside the vehicle compartment in order to effect switching between introduction of external air into the compartment and recirculation of air inside the compartment, and a system which detects contamination of air within a room caused by, for example smoking, and controls an air purifier.

Examples of such gas detection apparatuses utilizing a gas sensor element include a gas detection apparatus which detects a gas by means of differentiating a signal output from a gas sensor element; a gas detection apparatus in which a differentiated analog value is converted to a digital value, which is subjected to digital differentiation so as to obtain a second order derivative for detection of a gas; and a gas detection apparatus which detects a gas by comparing a sensor signal with an integral value obtained through integration of the sensor signal.

However, in gas detection apparatuses which utilize a gas sensor element whose electrical characteristics such as sensor resistance change in accordance with concentration of a specific gas, the electrical characteristics, such as the resistance, of the gas sensor element change in response to not only a change in concentration of the specific gas, but also other changes in the environment, such as changes in temperature, humidity, and wind velocity. Therefore, in a gas detection apparatus which utilizes differentiation so as to detect relative change of an output signal, wherein the output signal changes greatly in response to not only changes in concentration of the specific gas, but also other changes in the environment, such as temperature, humidity, and wind velocity, mere detection of relative change of the output signal fails to clearly distinguish the case in which such a change has occurred in response to a change in concentration of a specific gas from the case in which such a change has occurred in response to a disturbance such as a change in humidity. In the case in which a first order derivative or a second order derivative of the output signal of the gas sensor element is used as described above, a point in time at which gas concentration has changed, such as a point in time at which the gas concentration has suddenly increased, the change can be detected. However, difficulty is encountered in determining the amount by which the gas concentration has changed, or in determining a change in the gas concentration after that point in time and a later point in time at which the gas concentration decreases.

Meanwhile, in a gas detection apparatus which detects a gas by comparing a sensor signal with an integral value of the sensor signal, change in the integral value is delayed with respect to change in concentration of a specific gas. Therefore, in the case in which the gas detection apparatus is designed to increase its sensor output value with the gas concentration, once the concentration of the specific gas starts decreasing, there may arise a reverse state in which the integral value becomes greater than the sensor output value. Therefore, when the concentration of the specific gas increases after the above-described decrease, the gas detection apparatus fails to properly detect change in concentration of the specific gas (e.g., detection timing involves a delay), because the integral value is greater than the sensor output value having started increasing, with the result that the increase in concentration of the specific gas cannot be detected immediately.

Japanese Patent Application Laid-Open (kokai) No. H1-199142 discloses a gas detection apparatus which tracks change in a sensor output over time; stores, as a reference output, a sensor output corresponding to the cleanest atmosphere; after storage, gradually changes the reference output toward a side corresponding to a contaminated atmosphere; and when the changed reference output exceeds the actual sensor output, changes the reference output so as to correspond to the actual sensor output. In the invention, the rate of increase in the reference output is previously set to correspond to change in the sensor output caused by changes in temperature, humidity, etc., whereby gas detection is rendered possible even when temperature or humidity changes.

In the invention described in Japanese Patent Application Laid-Open No. H1-199142, the reference output is changed gradually at a constant rate with respect to time, irrespective of the magnitude of change in the sensor output. However, change in concentration of a specific gas is not constant and cannot be predicted. Take, for example, the case in which the gas concentration changes gradually toward the side corresponding to the contaminated atmosphere. In this case, when the set rate of increase in the reference output is high, the reference output becomes closer to the side corresponding to the contaminated atmosphere as compared with the sensor output, even though the sensor output also changes toward the side corresponding to the contaminated atmosphere, whereby the reference output is changed to correspond to the sensor output. Accordingly, even though the gas concentration has increased gradually to eventually reach a high level, such an increase in gas concentration cannot be detected correctly and quickly, because no difference is produced between the sensor output and the reference output.

Further, since the reference output is gradually changed; e.g., increased linearly, irrespective of the sensor output, the following problem may occur in the case in which a high gas concentration is maintained for a long period of time; e.g., in a long tunnel, so that a high sensor output is output continuously. In such a case, since the reference output gradually increases irrespective of the obtained sensor output, the difference between the sensor output and the reference output decreases, and eventually, the gas concentration is erroneously determined to be low.

SUMMARY OF THE INVENTION

Accordingly, the present invention is directed to a method of forming an insulating layer and a method of fabricating a thin film transistor using the same that substantially obviates one or more of the problems due to limitations and disadvantages of the related art.

An object of the present invention is to provide a gas detection apparatus that can detect an increase in gas concentration quickly and reliably; is not prone to erroneous determination; and is in an automatic ventilation system for a vehicle.

The present invention provides a gas detection apparatus using a gas sensor element whose electrical characteristics change in accordance with concentration of a specific gas, comprising: acquisition means for acquiring a sensor output value at predetermined cycle intervals by use of the gas sensor element, the sensor output value increasing with concentration of the specific gas; first calculation means for calculating a present first calculated value at the predetermined cycle intervals during a period in which a low-concentration signal is being generated, the present first calculated value representing a first calculated value at the present time and being calculated by use of a first calculation expression on the basis of a present sensor output value representing a sensor output value at the present time; the first calculation expression including a reference term including at least one of a tracking term which, while tracking the sensor output value, changes more slowly than does the sensor output value, and an increasing term which gradually increases irrespective of changes in the sensor output value, and an increase-emphasizing term using the present sensor output value and determined in such a manner that the present first calculated value calculated for a time series of sensor output values that are increasing monotonously becomes smaller than a virtual present first calculated value for the time series by use of a virtual first calculation expression obtained through omission of the increase-emphasizing term, and the present first calculated value decreases with the rate of increase in the sensor output values of the time series; and high-concentration-signal generation means for generating a high-concentration signal in place of the low-concentration signal when the present sensor output value and the present first calculated value satisfy a predetermined first relation during the period in which the low-concentration signal is being generated.

In the gas detection apparatus of the present invention, the acquisition means is configured in such a manner that the sensor output value increases with concentration of the specific gas. Further, the first calculation expression for calculating the present first calculated value has an increase-emphasizing term in addition to a reference term including at least either a tracking term or an increasing term. Therefore, when the sensor output value increases in response to, for example, an increased gas concentration, the present first calculated value calculated by use of the first calculation expression becomes smaller than a virtual present first calculated value calculated by use of a virtual first calculation expression obtained through omission of the increase-emphasizing term; i.e., including the tracking term or the increasing term only. Accordingly, when the high-concentration signal generation means determines whether the sensor output value and the present first calculated value satisfy a predetermined first relation by, for example, comparing with a threshold value the difference or ratio between the sensor output value and the present first calculated value, an increase in the sensor output value is emphasized as compared with the case in which the increase-emphasizing term is not present, so that an increase in the gas concentration can be detected quickly.

Incidentally, even when the gas concentration is maintained at a low level, the sensor output value may involve drift; i.e., may increase or decrease gradually, in response to disturbance such as a change in humidity or temperature. In particular, when the sensor output value drifts to thereby increase gradually, erroneous detection is apt to occur, because the sensor output value changes in a direction corresponding to increase in the gas concentration even though the gas concentration has not changed.

By contrast, in the gas detection apparatus of the present invention, the first calculation expression has an increase-emphasizing term in addition to a reference term including at least either a tracking term or an increasing term. In other words, the reference term and the increase-emphasizing term each contribute to the present first calculated value. Of these terms, the reference term produces a value which slowly increases to follow the sensor output value when the sensor output value gradually increases with time, or a value which gradually increases irrespective of changes in the sensor output value. The value calculated from the reference term changes in a direction such that the difference between the calculated value and the sensor output value does not increase even when the sensor output value increases because of drift. Therefore, erroneous detection caused by drift can be suppressed by use of the value calculated from the reference term.

Meanwhile, when the sensor output value gradually increases; i.e., when the rate of increase is low, the present first calculated value does not decrease very much, because of characteristics of the increase-emphasizing term. In other words, when the rate of increase is low, the contribution of the increase-emphasizing term to the present first calculated value decreases relative to the case in which the rate of increase is high. Therefore, in such a case, the contribution of the reference term to the present first calculated value increases, whereas the contribution of the increase-emphasizing term to the present first calculated value decreases. Accordingly, use of the present first calculated value, which has been greatly affected by the reference term as described above, prevents erroneous detection, which would otherwise occur because of drift of the sensor output value.

The increase-emphasizing term may be any term which uses the sensor output value and is determined in such a manner that the present first calculated value calculated for a time series of sensor output values that are increasing monotonously becomes smaller than a virtual present first calculated value for the time series by use of a virtual first calculation expression obtained through omission of the increase-emphasizing term. When the first calculation expression for calculating the present first calculated value $C1(n)$ is $C1(n)=C1(n-1)+k1[(S(n)-C1(n-1)]-k2[S(n)-S(n-q)]$, the term $-k2[S(n)-S(n-q)]$ serves as an increase-emphasizing term. When the first calculation expression for calculating the present first calculated value $C1(n)$ is $C1(n)=\{S(n)+S(n-1)+\ldots S(n-m)\}/m-k3[E-S(n)]$, the term $-k3[E-S(n)]$ serves as an increase-emphasizing term. In the above expressions, $S(n)$ represents a present sensor output value; $k1$, $k2$, and $k3$ are positive coefficients; $0<k1<1$; $n$, $m$, and $q$ are positive integers; and $E$ is a constant. Needless to say, the comparison between the virtual present first calculated value and the present first calculated value is performed after removal of an initial period corresponding to an initial portion of a given time series in which the increase-emphasizing term, etc. have not yet been calculated.

The tracking term of the reference term may be any term having characteristics such that the calculated value changes more slowly than does the present sensor output value, while tracking the present sensor output value. Examples of such a term include the above-mentioned term $C1(n-1)+k1[(S(n)-C1(n-1))$ for adding to the preceding first calculated value $C1(n-1)$ a value smaller than the difference $S(n)-C1(n-1)$ between the present sensor output $S(n)$ and the preceding first calculated value $C1(n-1)$, the above-mentioned term $\{S(n)+S(n-1)+ \ldots S(n-m)\}/m$ for providing a moving average value, and a term for providing an integral value.

In the present specification, the term "present value" refers to a latest value in a time series of values that are obtained successively; e.g., at predetermined cycle intervals; i.e., a value obtained at a point of time under consideration or the latest value among values obtained before that point of time. For example, the term "sensor output value at the present time (present sensor output value)" represents a sensor output value at a point of time under consideration (e.g., $S(n)$). Further, the term "first calculated value at the present time (present first calculated value)" represents a first calculated value at the point of time under consideration (e.g., $C1(n)$), and has one-to-one correspondence with the present sensor output value $S(n)$, because the two values are obtained in the same cycle.

Further, the term "past value" refers to a value obtained before the present value in the time series of values that are obtained successively; e.g., at predetermined cycle intervals. For example, the term "sensor output value in the past (past sensor output value)" represents a sensor output value obtained before the sensor output value under consideration (e.g., $S(n-1), S(n-2), \ldots$ for the present sensor output value $S(n)$). Further, the term "first calculated value in the past (past first calculated value)" represents a first calculated value calculated in the past (e.g., $C1(n-1), C1(n-2), \ldots$ for the present first calculated value $C1(n)$). Further, the past first calculated value $C1(n-1), C1(n-2)$, has one-to-one correspondence with the past sensor output value $S(n-1), S(n-2), \ldots$, because the two values are obtained in the same cycle.

Moreover, in the present specification, the term "preceding value" refers a value obtained immediately before the present value in the time series of values that are obtained successively at the predetermined cycle intervals. For example, the term "preceding sensor output value" represents a sensor output value obtained in a cycle preceding the cycle of the present sensor output value under consideration; i.e., a sensor output value obtained at a point in time which precedes, by the predetermined cycle interval, the point in time at which the present sensor output value under consideration was obtained (e.g., $S(n-1)$ is the preceding sensor value for $S(n)$). Further, the term "preceding first calculated value" represents a first calculated value obtained in the preceding cycle (e.g., $C1(n-1)$ for $C1(n)$).

Further, the high-concentration-signal generation means may be any means that generates a high-concentration signal; and the high-concentration signal may include a plurality of types of signals. Examples of the signals contained in the high-concentration signal include signals of different levels corresponding to a plurality of concentration levels (e.g. three concentration levels of +, ++, and +++), ranging from a relatively low concentration to a particularly high concentration, within a range of high concentration of a specific gas. These signals may be distinguished by a known method, such as a method in which the signals are made different in terms of signal voltage level or signal code.

Similarly, the low-concentration-signal generation means may be any means that generates a low-concentration signal; and the low-concentration signal may include a plurality of types of signals. Examples of the signals contained in the low-concentration signal include signals of different levels corresponding to a plurality of concentration levels ranging from a particularly low concentration level to a slightly high concentration level, within a range of low concentration of the specific gas.

The present invention according to claim 2 is a gas detection apparatus using a gas sensor element whose electrical characteristics change in accordance with concentration of a specific gas, comprising: acquisition means for acquiring a sensor output value at predetermined cycle intervals by use of the gas sensor element, the sensor output value increasing with concentration of the specific gas; first calculation means for calculating a present first calculated value at the predetermined cycle intervals during a period in which a low-concentration signal is being generated, the present first calculated value representing a first calculated value at the present time, wherein when a present sensor output value representing a sensor output value at the present time is greater than an $m^{th}$ past first calculated value representing the first calculated value calculated in a past cycle preceding the present cycle by m cycles, the first calculation means calculates the present first calculated value by use of a first calculation expression on the basis of the present sensor output value, the first calculation expression includes a reference term including at least one of a tracking term which, while tracking the sensor output value, changes more slowly than does the sensor output value, and an increasing term which gradually increases irrespective of changes in the sensor output value, and an increase-emphasizing term using the present sensor output value and determined in such a manner that the present first calculated value, calculated for a time series of sensor output values having an increase period in which the sensor output values increase monotonously and a decrease period subsequent to the increase period and in which the sensor output values decrease monotonously, becomes smaller, in the increase period, than a virtual present first calculated value for the time series by use of a virtual first calculation expression obtained through omission of the increase-emphasizing term, the present first calculated value decreasing with the rate of increase in the sensor output values of the time series, and, during the decrease period, the present first calculated value changing at a rate greater than a rate of change of the virtual present first calculated value, and when the present sensor output value is smaller than the $m^{th}$ past first calculated value, the first calculation means employs the present sensor output value as the present first calculated value; and high-concentration-signal generation means for generating a high-concentration signal in place of the low-concentration signal when the present sensor output value and the present first calculated value satisfy a predetermined first relation during the period in which the low-concentration signal is being generated.

In the gas detection apparatus of the present invention, the acquisition means is configured in such a manner that the sensor output value increases with concentration of the specific gas. Further, when the present sensor output value $S(n)$ is greater than the $m^{th}$ past first calculated value $C1(n-m)$; i.e., in the case where $S(n)>C1(n-m)$, the present first calculated value calculated by use of the first calculation expression is employed.

The first calculation expression has an increase-emphasizing term in addition to a reference term. Therefore, when the sensor output value increases in response to, for example, an increased gas concentration; i.e., in the case where S(n)>S(n−1), the present first calculated value calculated by use of the first calculation expression becomes smaller than a virtual present first calculated value calculated by use of a virtual first calculation expression obtained through omission of the increase-emphasizing term; i.e., including the tracking term or the increasing term only. Accordingly, when the high-concentration signal generation means determines whether the sensor output value and the present first calculated value satisfy a predetermined first relation by, for example, comparison between a threshold value and the difference or ratio between the sensor output value and the present first calculated value, an increase in the sensor output value is emphasized as compared with the case in which the increase-emphasizing term is not present, so that an increase in the gas concentration can be detected quickly.

Incidentally, in the case where, unlike the case of the present invention, the present first calculated value is calculated by use of the above-described first calculation expression irrespective of whether the present sensor output value S(n) is greater than the $m^{th}$ past first calculated value C1(n−m) and is used continuously, when the sensor output value S(n) decreases, the present first calculated value C1(n) increases relatively, and in some cases, there may arise a reverse state in which the relation C1(n)>S(n), which is the reverse of the previous relation, is established. In such a case, even when the sensor output value S(n) increases in response to an increase in the gas concentration after the above-described decrease, the first relation; e.g., the difference between the sensor output value and the present first calculated value being greater than a threshold (S(n)−C1(n)> SH, where SH is the threshold value), becomes difficult to satisfy, so that gas detection may involve a delay.

In the present invention, when S(n)<C1(n−m), the relation C1(n)=S(n) is forcibly established, whereby the reverse state (C1(n)>S(n)) is eliminated. Therefore, when the concentration subsequently increases, the sensor output value increases, and the present first calculated value changes from the value equal to the present sensor output value (C1(n)= S(n)) and becomes smaller than the virtual present first calculated value, which slowly increases or follows the sensor output value, whereby the first relation, such as a predetermined difference or ratio between the sensor output value and the present first calculated value can be attained quickly, and hence the gas can be detected quickly.

Notably, the "predetermined number (m) of cycles" in the $m^{th}$ past first calculated value C1(n−m) may be determined in consideration of the responsiveness of a gas sensor element to be used, cycle interval (sampling period), magnitudes of disturbances such as changes in humidity or temperature, and the shortest period of variation caused thereby. However, in general, the predetermined number m is set to a small value, preferably to a value not greater than 2 or 3, more preferably to one. That is, preferably, the preceding first calculated value C1(n−1) is used.

The present invention according to claim 3 is a gas detection apparatus using a gas sensor element whose electrical characteristics change in accordance with concentration of a specific gas, comprising: acquisition means for acquiring a sensor output value at predetermined cycle intervals by use of the gas sensor element, the sensor output value decreasing as concentration of the specific gas increases; first calculation means for calculating a present first calculated value at the predetermined cycle intervals during a period in which a low-concentration signal is being generated, the present first calculated value representing a first calculated value at the present time and being calculated by use of a first calculation expression on the basis of a present sensor output value representing a sensor output value at the present time; the first calculation expression including a reference term including at least one of a tracking term which, while tracking the sensor output value, changes more slowly than does the sensor output value, and a decreasing term which gradually decreases irrespective of changes in the sensor output value, and a decrease-emphasizing term using the present sensor output value and determined in such a manner that the present first calculated value calculated for a time series of sensor output values that are decreasing monotonously becomes greater than a virtual present first calculated value for the time series by use of a virtual first calculation expression obtained through omission of the decrease-emphasizing term, and the present first calculated value increases with the rate of decrease in the sensor output values of the time series; and high-concentration-signal generation means for generating a high-concentration signal in place of the low-concentration signal when the present sensor output value and the present first calculated value satisfy a predetermined first relation during the period in which the low-concentration signal is being generated.

In the gas detection apparatus of the present invention, the acquisition means is configured in such a manner that the sensor output value decreases as concentration of the specific gas increases. Further, the first calculation expression has a decrease-emphasizing term in addition to a reference term including at least either a tracking term or an increasing term. Therefore, when the sensor output value decreases in response to, for example, an increased gas concentration, the present first calculated value calculated by use of the first calculation expression becomes greater than a virtual present first calculated value calculated by use of a virtual first calculation expression obtained through omission of the decrease-emphasizing term; i.e., including the tracking term or the decreasing term only. Accordingly, when the high-concentration signal generation means determines whether the sensor output value and the present first calculated value satisfy a predetermined first relation by, for example, comparing with a threshold value the difference or ratio between the sensor output value and the present first calculated value, a decrease in the sensor output value is emphasized as compared with the case in which the decrease-emphasizing term is not present, so that an increase in the gas concentration can be detected quickly.

Incidentally, even when the gas concentration is maintained at a low level, the sensor output value may involve a drift; i.e., may increase or decrease gradually, in response to disturbance such as a change in humidity or temperature. In particular, when the sensor output value drifts to thereby decrease gradually, erroneous detection is apt to occur, because the sensor output value changes in a direction corresponding to increase in the gas concentration even though the gas concentration has not changed.

By contrast, in the gas detection apparatus of the present invention, the first calculation expression has a decrease-emphasizing term in addition to a reference term including at least either a tracking term or a decreasing term. Of these terms, the reference term produces a value which slowly decreases to follow the sensor output value when the sensor output value gradually decreases with time, or a value which gradually decreases irrespective of changes in the sensor output value. Meanwhile, when the sensor output value gradually decreases; i.e., when the rate of decrease is low, the present first calculated value does not increase very much, because of characteristics of the decrease-emphasizing term. In other words, when the rate of decrease is low, the contribution of the decrease-emphasizing term to the present first calculated value decreases relative to the case in which the rate of decrease is high. Therefore, the contribution of the reference term to the present first calculated value increases. Accordingly, use of the present first calculated value, which has been affected by the reference term as described above, prevents erroneous detection, which would otherwise occur because of drift of the sensor output value.

The decrease-emphasizing term may be any term which uses the sensor output value and is determined in such a manner that the present first calculated value calculated for a time series of sensor output values that are decreasing monotonously becomes greater than a virtual present first calculated value for the time series by use of a virtual first calculation expression obtained through omission of the decrease-emphasizing term. When the first calculation expression for calculating the present first calculated value $C1(n)$ is $C1(n)=C1(n-1)+k5[S(n)-C1(n-1)]-k6[S(n)-S(n-t)]$, the term $-k6[S(n)-S(n-t)]$ serves as a decrease-emphasizing term. When the first calculation expression for calculating the present first calculated value $C1(n)$ is $C1(n)=\{S(n)+S(n-1)+ \ldots S(n-m)\}/m-k7[E-S(n)]$, the term $-k7[E-S(n)]$ serves as a decrease-emphasizing term. In the above expressions, $S(n)$ represents a present sensor output value; $k5$, $k6$, and $k7$ are positive coefficients; $0<k5<1$; $n$, $m$, and $t$ are positive integers; and $E$ is a constant. Needless to say, the comparison between the virtual present first calculated value and the present first calculated value is performed after removal of an initial period corresponding to an initial portion of a given time series in which the decrease-emphasizing term, etc. have not yet been calculated.

The present invention according to claim 4 is a gas detection apparatus using a gas sensor element whose electrical characteristics change in accordance with concentration of a specific gas, comprising: acquisition means for acquiring a sensor output value at predetermined cycle intervals by use of the gas sensor element, the sensor output value decreasing as concentration of the specific gas increases; first calculation means for calculating a present first calculated value at the predetermined cycle intervals during a period in which a low-concentration signal is being generated, the present first calculated value representing a first calculated value at the present time, wherein when a present sensor output value representing a sensor output value at the present time is smaller than an $m^{th}$ past first calculated value representing the first calculated value calculated in a past cycle preceding the present cycle by m cycles, the first calculation means calculates the present first calculated value by use of a first calculation expression on the basis of the present sensor output value, the first calculation expression includes a reference term including at least one of a tracking term which, while tracking the sensor output value, changes more slowly than does the sensor output value, and a decreasing term which gradually decreases irrespective of changes in the sensor output value, and a decrease-emphasizing term using the present sensor output value and determined in such a manner that the present first calculated value, calculated for a time series of sensor output values having a decrease period in which the sensor output values decrease monotonously and an increase period subsequent to the decrease period and in which the sensor output values increase monotonously, becomes greater, in the decrease period, than a virtual present first calculated value for the time series by use of a virtual first calculation expression obtained through omission of the decrease-emphasizing term, the present first calculated value increasing with the rate of decrease in the sensor output values of the time series, and, during the increase period, the present first calculated value changing at a rate smaller than a rate of change of the virtual present first calculated value, and when the present sensor output value is greater than the $m^{th}$ past first calculated value, the first calculation means employs the present sensor output value as the present first calculated value; and high-concentration-signal generation means for generating a high-concentration signal in place of the low-concentration signal when the present sensor output value and the present first calculated value satisfy a predetermined first relation during the period in which the low-concentration signal is being generated.

In the gas detection apparatus of the present invention, the acquisition means is configured in such a manner that the sensor output value decreases as the concentration of the specific gas increases. Further, when the present sensor output value $S(n)$ is smaller than the $m^{th}$ past first calculated value $C1(n-m)$; i.e., in the case where $S(n)<C1(n-m)$, the present first calculated value calculated by use of the first calculation expression is employed.

The first calculation expression has a decrease-emphasizing term in addition to a reference term. Therefore, when the sensor output value decreases in response to, for example, an increased gas concentration; i.e., in the case where $S(n)<S(n-1)$, the present first calculated value calculated by use of the first calculation expression becomes greater than a virtual present first calculated value calculated by use of a virtual first calculation expression obtained through omission of the decrease-emphasizing term; i.e., including the tracking term or the decreasing term only. Accordingly, when the high-concentration signal generation means determines whether the sensor output value and the present first calculated value satisfy a predetermined first relation by, for example, comparison between a threshold value and the difference or ratio between the sensor output value and the present first calculated value, a decrease in the sensor output value is emphasized as compared with the case in which the decrease-emphasizing term is not present, so that an increase in the gas concentration can be detected quickly.

Incidentally, in the case where, unlike the case of the present invention the present first calculated value is calculated by use of the above-described first calculation expression irrespective of whether the present sensor output value $S(n)$ is greater than the $m^{th}$ past first calculated value $C1(n-m)$ and is used continuously, when the sensor output value $S(n)$ increases, the present first calculated value $C1(n)$ decreases relatively, and in some cases, there may arise a reverse state in which the relation $C1(n)<S(n)$, which is reverse of the previous relation, is established. In such a case, even when the sensor output value $S(n)$ decreases in response to an increase in the gas concentration after the above-described decrease, the first relation; e.g., the difference between the sensor output value and the present first calculated value being greater than a threshold ($C1(n)-S(n)>SH$, where $SH$ is the threshold value), becomes difficult to satisfy, so that gas detection may involve a delay.

In the present invention, when $S(n)>C1(n-m)$, the relation $C1(n)=S(n)$ is forcibly established, whereby the reverse state ($C1(n)<S(n)$) is eliminated. Therefore, when the concentration subsequently increases, the sensor output value decreases, and the present first calculated value changes from the value equal to the present sensor output value (C1(n)=S(n)) and becomes greater than the virtual present first calculated value, which slowly decreases or follows the sensor output, whereby the first relation, such as a predetermined difference or ratio between the sensor output value and the present first calculated value can be attained quickly, and hence the gas can be detected quickly.

Notably, although the "predetermined number (m) of cycles" in the mth past first calculated value C1(n−m) may be determined arbitrarily, in general, the predetermined number m is set to a small value, preferably to a value not greater than 2 or 3, more preferably to one; i.e., the preceding first calculated value C1(n−1) is used.

In the gas detection apparatus according to claim 2 or 4, the $m^{th}$ past first calculated value is preferably a preceding first calculated value calculated in a preceding cycle. In the gas detection apparatus, the preceding first calculated value is used as the $m^{th}$ past first calculated value. In the case in which the predetermined cycle number m is 2 or greater, when the relation S(n)>C1(n−m) is established, the relation C1(n)=S(n) is forcibly established, and therefore, in some periods, a reversed relation in terms of magnitude arises between the past first calculated values C1(n−1), C1(n−2), . . . , C1(n−m+1), etc. and the corresponding past sensor output values S(n−1), S(n−2), . . . , S(n−m+1), etc. In the case of the invention according to claim 2, the past first calculated value C1(n−p), where p is a positive integer not greater than m, may become greater than the corresponding past sensor output value S(n−p); i.e., the relation C1(n−p)>S(n−p) may be established in some periods. In the case of the invention according to claim 4, the past first calculated value C1(n−p) may become smaller than the corresponding past sensor output value S(n−p); i.e., the relation C1(n−p)<S(n−p) may be established in some periods. During such reverse state periods, an increase in concentration of the specific gas becomes difficult to detect.

In the case of the present invention in which m is set to 1; i.e., in which the first calculation means compares the preceding first calculated value C1(n−1) with the present sensor output value S(n), the reverse state does not arise, and therefore, an increase in concentration of the specific gas can be detected more quickly.

Moreover, determination as to whether the present first calculated value C1(n) is to be calculated newly or the present sensor output value S(n) is to be employed as the present first calculated value C1(n) is performed through comparison between the preceding first calculated value C1(n−1) and the present sensor output value S(n). Therefore, the number of the first calculated values to be stored can be decreased so as to reduce the consumed memory area.

The gas detection apparatus according to any one of claims 1 to 6 may comprise second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated. In the gas detection apparatus of the present invention, the low-concentration signal is generated in place of the high-concentration signal when the second calculated value calculated by use of the present sensor output value satisfies the second relation; e.g., when the difference between the sensor output value and the present second calculated value is greater than a threshold (S(n)−C2(n)>SH, where SH is the threshold value).

Accordingly, the determination performed for switching from the high-concentration signal to the low-concentration signal is performed by use of the second calculated value which reflects the sensor output value, whereby the switching can be performed properly.

Notably, any calculation expression may be used for calculating the second calculated value, so long as the chosen expression can reflect change in the sensor output value. Examples of such an expression include an expression for providing a moving average value; an expression for providing an integral value; an expression C2(n)=C2(n−1)+ka[S(n)−C2(n−1)], where 0<ka<1; an expression C2(n)=C2(n−1)+ka[S(n)−C2(n−1)]−kb[(S(n)−S(n−r)], where 0<ka<1, kb>0, and r is a positive integer); and an expression for providing a first order derivative or a second order derivative.

The gas detection apparatus according to claim 1 or 2 may comprise second calculation means for calculating a present second calculated value by use of the present sensor output value at the predetermined cycle intervals during a period in which the high-concentration-signal generation means is generating the high-concentration signal, the present second calculated value representing a second calculated value at the present time, and the second calculation means calculating the present second calculated value by use of a second calculation expression including a second reference term including at least one of a second tracking term which, while tracking the sensor output value, changes more slowly than does the sensor output value, and a second increasing term which gradually increases irrespective of changes in the sensor output value, and a second increase-emphasizing term using the present sensor output value and determined in such a manner that the present second calculated value calculated for a time series of sensor output values having an increase period in which the sensor output values increase monotonously and a decrease period which is subsequent to the increase period and in which the sensor output values decrease monotonously, becomes smaller, in the increase period, than a virtual present second calculated value for the time series by use of a virtual second calculation expression obtained through omission of the second increase-emphasizing term, the present second calculated value decreasing with the rate of increase in the sensor output values of the time series, and, during the decrease period, the present second calculated value changing at a rate greater than a rate of change of the virtual present second calculated value; and low-concentration-signal generation means for generating the low-concentration signal in place of the high-concentration signal when the present sensor output value and the present second calculated value satisfy a predetermined second relation during the period in which the high-concentration signal is being generated.

In the gas detection apparatus of the present invention, as in the case of the gas detection apparatus according to claim 1 or 2, the acquisition means is configured in such a manner that the sensor output value increases with concentration of the specific gas. Further, the present second calculated value is calculated by use of the second calculation expression consisting of a second reference term and a second increase-emphasizing term. The second reference term includes at least one of a second tracking term which, while tracking the sensor output value, changes more slowly than does the sensor output value, and a second increasing term which gradually increases irrespective of changes in the sensor output value.

In an assumed case in which the virtual present second calculated value is calculated by use of a second calculation expression consisting of the second reference term only (i.e., the second increase-emphasizing term is not present), when gas concentration gradually increases over a long period of time or the gas concentration is maintained high over a long period of time; e.g., in a long tunnel or an underground parking area, the virtual present second calculated value approaches the present sensor output value during a period in which the high-concentration signal is being generated. In such a case, when the present sensor output value drops temporarily because of noise or other causes, the difference or ratio between these values decreases, and the gas concentration may be erroneously detected to have dropped.

In view of the above, the second calculation expression used in the present invention has a second increase-emphasizing term. This second increase-emphasizing term is determined in such a manner that the present second calculated value calculated for a time series of sensor output values having an increase period in which the sensor output values increase monotonously and a decrease period which is subsequent to the increase period and in which the sensor output values decrease monotonously, becomes smaller, in the increase period, than a virtual present second calculated value for the time series calculated by use of a virtual second calculation expression obtained through omission of the second increase-emphasizing term, the present second calculated value decreasing with the rate of increase in the sensor output values of the time series. Further, during the decrease period, the present second calculated value changes at a rate greater than a rate of change of the virtual present second calculated value.

Therefore, by virtue of the presence of the second increase-emphasizing term, during a period in which the gas concentration increases after the low-concentration signal is switched to the high-concentration signal, whereby the sensor output value rises (increases), the present second calculated value becomes smaller than the virtual present second calculated value. In other words, there is established a state in which the difference or ratio between the sensor output value and the present second calculated value is greater than the difference or ratio between the sensor output value and the virtual present second calculated value. Therefore, when the sensor output value drops temporarily because of noise, although the difference or ratio between these values decreases temporarily, the difference or ratio does not become smaller than a threshold, thereby preventing erroneous detection.

Further, when the gas concentration drops after the increase and thus the sensor output value decreases, the present second calculated value changes at a rate greater than a rate of change of the virtual present second calculated value. Therefore, as the sensor output value drops, the present second calculated value, which before the drop in the gas concentration was smaller than the virtual present second calculated value, changes at a rate greater than a rate of change of the virtual present second calculated value. As a result, the difference between the sensor output value and the present second calculated value decreases quickly. In some cases, the present second calculated value becomes greater than the sensor output value (a reverse state). Accordingly, the drop in the gas concentration can be detected immediately upon satisfaction of the second relation; e.g., when the difference between the sensor output value and the present second calculated value becomes lower than the threshold.

That is, when the present second calculated value obtained by use of the second calculation expression of the present invention is used, a slight drop in the sensor output value attributable to noise or other causes is not erroneously detected to be a concentration drop, but a large drop or continuous drop in the sensor output value can be immediately detected as a concentration drop. Accordingly, such a large or continuous concentration drop can be detected reliably and quickly.

The gas detection apparatus according to claim 3 or 4 may comprise second calculation means for calculating a present second calculated value by use of the present sensor output value at the predetermined cycle intervals during a period in which the high-concentration-signal generation means is generating the high-concentration signal, the present second calculated value representing a second calculated value at the present time, and the second calculation means calculating the present second calculated value by use of a second calculation expression including a second reference term including at least one of a second tracking term which, while tracking the sensor output value, changes more slowly than does the sensor output value, and a second decreasing term which gradually decreases irrespective of changes in the sensor output value, and a second decrease-emphasizing term using the present sensor output value and determined in such a manner that the present second calculated value calculated for a time series of sensor output values having a decrease period in which the sensor output values decrease monotonously and an increase period which is subsequent to the decrease period and in which the sensor output values increase monotonously, becomes greater, in the decrease period, than a virtual present second calculated value for the time series by use of a virtual second calculation expression obtained through omission of the second decrease-emphasizing term, the present second calculated value increasing with the rate of decrease in the sensor output values of the time series, and, during the increase period, the present second calculated value changing at a rate smaller than a rate of change of the virtual present second calculated value; and low-concentration-signal generation means for generating the low-concentration signal in place of the high-concentration signal when the present sensor output value and the present second calculated value satisfy a predetermined second relation during the period in which the high-concentration signal is being generated.

In the gas detection apparatus of the present invention, as in the case of the gas detection apparatus according to claim 3 or 4, the acquisition means is configured in such a manner that the sensor output value decrease when the concentration of the specific gas increases. Further, the present second calculated value is calculated by use of the second calculation expression consisting of a second reference term and a second decrease-emphasizing term. The second reference term includes at least one of a second tracking term which, while tracking the sensor output value, changes more slowly than does the sensor output value, and a second decreasing term which gradually decreases irrespective of changes in the sensor output value.

In an assumed case in which the virtual present second calculated value is calculated by use of a second calculation expression consisting of the second reference term only (i.e., the second decrease-emphasizing term is not present), when gas concentration gradually increases over a long period of time or the gas concentration is maintained high over a long period of time; e.g., in a long tunnel or an underground parking area, the virtual present second calculated value approaches the present sensor output value in a period in which the high-concentration signal is being generated. In such a case, when the virtual present sensor output value increases temporarily because of noise or other causes, the difference or ratio between these values decreases, and the gas concentration may be erroneously detected to have dropped.

In view of the above, the second calculation expression used in the present invention has a second decrease-emphasizing term. This second decrease-emphasizing term is determined in such a manner that the present second calculated value calculated for a time series of sensor output values having a decrease period in which the sensor output values decrease monotonously and an increase period which is subsequent to the decrease period and in which the sensor output values increase monotonously, becomes greater, in the decrease period, than a virtual present second calculated value for the time series calculated by use of a virtual second calculation expression obtained through omission of the second decrease-emphasizing term, the present second calculated value increasing with the rate of decrease in the sensor output values of the time series. Further, during the increase period, the present second calculated value changes at a rate smaller than a rate of change of the virtual present second calculated value.

Therefore, by virtue of the presence of the second decrease-emphasizing term, during a period in which the gas concentration increases after the low-concentration signal is switched to the high-concentration signal, whereby the sensor output value drops (decreases), the present second calculated value becomes greater than the virtual present second calculated value. In other words, there is established a state in which the difference or ratio between the present second calculated value and the sensor output value is greater than the difference or ratio between the virtual present second calculated value and the sensor output value. Therefore, when the sensor output value increases temporarily because of noise, although the difference or ratio between these values decreases temporarily, the difference or ratio does not become smaller than a threshold, thereby preventing erroneous detection.

Further, when the gas concentration decreases after the increase and thus the sensor output value increases, the present second calculated value changes at a rate smaller than a rate of change of the virtual present second calculated value. Therefore, as the sensor output value increases, the present second calculated value, which before the drop of the gas concentration was greater than the virtual present second calculated value, changes at a rate smaller than a rate of change of the virtual present second calculated value. As a result, the difference between the sensor output value and the present second calculated value decreases quickly. In some cases, the present second calculated value becomes smaller than the sensor output value (a reverse state). Accordingly, the drop in the gas concentration can be detected immediately upon satisfaction of the second relation; e.g., when the difference between the present second calculated value and the sensor output value becomes lower than the threshold.

That is, when the present second calculated value obtained by use of the second calculation expression of the present invention is used, a slight rise in the sensor output value attributable to noise or other causes is not erroneously detected to be a concentration drop, but a large increase or continuous increase in the sensor output value can be immediately detected as a concentration drop. Accordingly, such a large or continuous concentration drop can be detected reliably and quickly.

The present invention according to claim 17 is a gas detection apparatus using a gas sensor element whose electrical characteristics change in accordance with concentration of a specific gas, comprising: acquisition means for acquiring a sensor output value $S(n)$ at predetermined cycle intervals by use of the gas sensor element, the sensor output value $S(n)$ increasing with concentration of the specific gas, where n is an integer representing the chronological order of each sensor output value in a time series of sensor output values; first base-value calculation means for calculating a base value $B(n)$ at the predetermined cycle intervals during a period in which a low-concentration signal is being generated, the base value $B(n)$ being calculated in accordance with Expression (1):

$$B(n)=B(n-1)+k1[S(n)-B(n-1)]-k2[S(n)-S(n-q)] \qquad (1)$$

where k1 and k2 are first and second coefficients, $0<k1<1$, $K2>0$, and q is a positive integer; differential-value calculation means for calculating a difference value $D(n)$ in accordance with Expression (2):

$$D(n)=S(n)-B(n) \qquad (2)$$

on the basis of the sensor output value $S(n)$ and the base value $B(n)$; and high-concentration-signal generation means for generating a high-concentration signal when the difference value $D(n)$ is greater than a high-concentration threshold Tu.

First, the base value $B(n)$ will be described. The term $B(n-1)+k1[S(n)-B(n-1)]$ of Expression (1) is a tracking term which changes more slowly than does the sensor output value $S(n)$, while tracking the sensor output value $S(n)$. This tracking term has characteristics such that when the value of the coefficient k1 is changed, the speed of tracking or following the sensor output value $S(n)$ (i.e., sensitivity) changes. When the coefficient k1 increases (approaches 1), the tracking term follows the sensor output value $S(n)$ more quickly with higher sensitivity. By contrast, when the coefficient k1 decreases (approaches 0), the rate of change of the value of the tracking term decreases, so that the value of the tracking term follows the sensor output value $S(n)$ slowly. Meanwhile, the term $-k2[S(n)-S(n-q)]$ is an increase-emphasizing term for calculating a derivative. For example, when the present sensor output value $S(n)$ increases from the $q^{th}$ past sensor output value $S(n-q)$; i.e., in the case where $S(n)>S(n-q)$, the base value $B(n)$ becomes smaller than a virtual base value which is calculated by use of the above-described tracking term only without use of the increase-emphasizing term.

In the gas detection apparatus of the present invention, the acquisition means is configured in such a manner that the sensor output value $S(n)$ increases with concentration of the specific gas. In the gas detection apparatus, the first base-value calculation means calculates the base value $B(n)$ during a period in which the low-concentration signal is being generated. Further, the differential-value calculation means calculates a difference value $D(n)$; and the high-concentration-signal generation means generates a high-concentration signal in place of the low-concentration signal when the difference value $D(n)$ is greater than a high-concentration threshold Tu; i.e., in the case where $D(n)=S(n)-B(n)>Tu$. Specifically, during a period in which the low-concentration signal is being generated, the first base-value calculation means calculates a new base value $B(n)$ by use of the above-described Expression (1).

As described above, when the sensor output value $S(n)$ increases, the virtual base value which is calculated by use of the tracking term only without use of the increase-emphasizing term changes more slowly than does the sensor output value S(n), while tracking the sensor output value S(n). Meanwhile, the base value B(n) calculated by use of Expression (1) including the increase-emphasizing term becomes smaller than the virtual base value. Accordingly, the difference value D(n) calculated by use of Expression (2) becomes greater than a virtual difference value representing the difference between the sensor output value and the virtual base value. As a result, as compared with the virtual difference value, the difference value D(n) is more apt to exceed the high-concentration threshold Tu. In other words, an increase in the sensor output value resulting from an increase in the gas concentration can be detected quickly to thereby generate the high-concentration signal.

Further, in Expression (1), as described above, the value calculated by means of the tracking term changes more slowly than does the sensor output value S(n), while following the sensor output value S(n). Therefore, there can be prevented the situation where the gas concentration is erroneously detected to have increased by the influence of drift such as change in temperature or humidity, to thereby enable reliable gas detection.

The present invention according to claim 18 is a gas detection apparatus using a gas sensor element whose electrical characteristics change in accordance with concentration of a specific gas, comprising: acquisition means for acquiring a sensor output value S(n) at predetermined cycle intervals by use of the gas sensor element, the sensor output value S(n) increasing with concentration of the specific gas, where n is an integer representing the chronological order of each sensor output value in a time series of sensor output values; first base-value calculation means for calculating a base value B(n) at the predetermined cycle intervals during a period in which a low-concentration signal is being generated, wherein when the sensor output value S(n) is greater than a preceding base value B(n−1) representing a base value calculated in a preceding cycle, the first base-value calculation means calculates the base value B(n) in accordance with Expression (1):

$$B(n)=B(n-1)+k1[S(n)-B(n-1)]-k2[S(n)-S(n-q)] \quad (1)$$

where k1 and k2 are first and second coefficients, 0<k1<1, K2>0, and q is a positive integer, and when the sensor output value S(n) is smaller than the preceding base value B(n−1), the first base-value calculation means calculates the base value B(n) in accordance with Expression (3): B(n)=S(n) (3) differential-value calculation means for calculating a difference value D(n) in accordance with Expression (2):

$$D(n)=S(n)-B(n) \quad (2)$$

on the basis of the sensor output value S(n) and the base value B(n); and high-concentration-signal generation means for generating a high-concentration signal when the difference value D(n) is greater than a high-concentration threshold Tu.

The characteristics of the base value obtained by use of Expression (1) has already been described. In the gas detection apparatus of the present invention, the acquisition means is configured in such a manner that the sensor output value S(n) increases with concentration of the specific gas. In the gas detection apparatus, the first base-value calculation means calculates the base value B(n) during a period in which the low-concentration signal is being generated. Further, the differential-value calculation means calculates a difference value D(n); and the high-concentration-signal generation means generates a high-concentration signal in place of the low-concentration signal when the difference value D(n) is greater than a high-concentration threshold Tu; i.e., in the case where D(n)=S(n)−B(n)>Tu.

Specifically, during a period in which the low-concentration signal is being generated, the first base-value calculation means calculates a new base value B(n) by use of Expression (5) when a newly acquired sensor output value S(n) is greater than a preceding base value B(n−1).

As described above, when the sensor output value S(n) increases, the virtual base value which is calculated by use of Expression (1) with the third term (the increase-emphasizing term) deleted; i.e., the value calculated by use of the first term and the second term (tracking term) only, changes more slowly than does the sensor output value S(n), while tracking the sensor output value S(n). Meanwhile, the base value B(n) calculated by use of Expression (1) including the increase-emphasizing term becomes smaller than the virtual base value. Accordingly, the difference value D(n) calculated by use of Expression (2) becomes greater than a virtual difference value representing the difference between the sensor output value and the virtual base value. As a result, as compared with the virtual difference value, the difference value D(n) is more apt to exceed the high-concentration threshold Tu. In other words, an increase in the sensor output value resulting from an increase in the gas concentration can be detected quickly to thereby generate the high-concentration signal.

Further, in Expression (1), as described above, the value calculated by means of the tracking term changes more slowly than does the sensor output value S(n), while following the sensor output value S(n). Therefore, there can be prevented the situation where the gas concentration is erroneously detected to have increased by the influence of drift such as change in temperature or humidity, to thereby enable reliable gas detection.

Meanwhile, when the sensor output value S(n) is smaller than the preceding base value B(n−1), the first base-value calculation means calculates the base value B(n) by use of Expression (3). In other words, the present sensor output value S(n) is used as the base value B(n). Through this operation, the newly calculated base value B(n) is forcibly made equal to the sensor output value S(n), irrespective of the magnitude of the preceding base value B(n−1).

Therefore, when the sensor output value S(n) becomes smaller than the preceding sensor output value S(n−1) in the next cycle (after passage of the predetermined cycle interval), the relation S(n)<B(n−1) (=S(n−1)) is satisfied, and therefore the present sensor output value S(n) is used as the base value B(n). Therefore, during a period in which the relation of the sensor output value S(n) being smaller than the preceding sensor output value S(n−1) continues, the sensor output value S(n) is equal to the base value B(n). That is, the base value B(n) changes to assume the same magnitude as that of the sensor output value S(n).

At the point in time when the gas concentration starts to increase and the sensor output value becomes greater than the preceding value; i.e., when the relation S(n)>S(n−1) (=B(n−1)) is satisfied, the sensor output value S(n) becomes greater than the preceding base value B(n−1), and therefore, the calculation of the base value B(n) by use of Expression (1) is started. Accordingly, a positive difference (Dn) is generated between the sensor output value S(n) and the base value B(n); and when the difference (Dn) becomes greater than the high-concentration threshold Tu, so that the high-concentration signal is generated in place of the low-concentration signal. As described above, an increase in the gas concentration can be detected quickly, irrespective of changes in the base value B(n) in the past; i.e., irrespective of changes in the gas concentration in the past.

The gas detection apparatus according to claim 17 or 18 preferably comprises: second base-value calculation means for calculating a base value B(n) in accordance with Expression (4) at the predetermined cycle intervals during a period in which the high-concentration signal is being generated:

$$B(n)=B(n-1)+k3[S(n)-B(n-1)]-k4[S(n)-S(n-r)] \quad (4)$$

where k3 and k4 are third and fourth coefficients, 0<k3<1, K4>0, and r is a positive integer; and low-concentration-signal generation means for generating a low-concentration signal when the difference value D(n) is smaller than a low-concentration threshold Td.

In the gas detection apparatus, the second base-value calculation means calculates the base value by use of Expression (4) during a period in which the high-concentration signal is being generated. The base value calculated by use of Expression (4) has the same characteristics as do those of the base value calculated by use of Expression (1). That is, the term B(n-1)+k3[S(n)-B(n-1)] of Expression (4) is a second tracking term which changes more slowly than does the sensor output value S(n) while following the sensor output value S(n).

Meanwhile, the term -k4[S(n)-S(n-r)] is a second increase-emphasizing term for calculating a derivative. When the present sensor output value S(n) increases from the $r^{th}$ past sensor output value S(n-r); i.e., in the case where S(n)>S(n-r), the base value B(n) becomes smaller than a virtual base value which is calculated by use of the above-described second tracking term only and without use of the second increase-emphasizing term. Further, when the sensor output value decreases after the increase and the present sensor output value S(n) becomes smaller than the $r^{th}$ past sensor output value S(n-r); i.e., in the case where S(n)<S(n-r), the second increase-emphasizing term produces a positive value. As a result, as compared with the virtual base value, the base value B(n) approaches the sensor output value S(n) more quickly.

During a period in which the high-concentration signal is being generated, the gas detection apparatus of the present invention calculates such a base value B(n) by use of the second base-value calculation means. Further, the low-concentration-signal generation means generates the low-concentration signal in place of the high-concentration signal when the difference value D(n) is smaller than the low-concentration threshold Td; i.e., in the case where D(n)=S(n)-B(n)<Td. Specifically, during a period in which the high-concentration signal is being generated, the second base-value calculation means calculates a new base value B(n) by use of the above-described Expression (4).

As described above, when the sensor output value S(n) increases, the virtual base value which is calculated by use of Expression (4) with the second increase-emphasizing term omitted; i.e., the value calculated by use of the second tracking term only, changes more slowly than does the sensor output value S(n), while tracking the sensor output value S(n). Meanwhile, the base value B(n) calculated by use of Expression (4) including the second increase-emphasizing term becomes smaller than the virtual base value. Accordingly, during a period in which the gas concentration increases after the low-concentration signal is switched to the high-concentration signal, whereby the sensor output value S(n) rises, the base value B(n) becomes smaller than the virtual base value, by virtue of the presence of the second increase-emphasizing term in Expression (4).

Therefore, when the sensor output value drops temporarily in response to noise during a period in which the gas concentration is high, the difference value D(n) does not become smaller than the low-concentration threshold Td, whereby an erroneous operation of generating the low-concentration signal can be prevented.

Meanwhile, when the sensor output value drops in response to a decrease in the gas concentration, as described above, the base value B(n) approaches the sensor output value S(n) quickly. As a result, the difference value D(n) becomes smaller than the low-concentration threshold Td, and thus the decrease in the gas concentration can be detected quickly to thereby generate the low-concentration signal.

Preferably, the $q^{th}$ past sensor output value S(n-q) used in the increase-emphasizing term is used in the second increase-emphasizing term as the $r^{th}$ past sensor output value S(n-r); i.e., r=q. This can reduce the number of past sensor output values to be stored and reduce the program load through use of a common expression. Further, abrupt change in the base value can be avoided, which change would otherwise occur when the cycle number of the past sensor output value used in the calculation changes upon switching between the high-concentration signal and the low-concentration signal.

The present invention according to claim 21 is a gas detection apparatus using a gas sensor element whose electrical characteristics change in accordance with concentration of a specific gas, comprising: acquisition means for acquiring a sensor output value S(n) at predetermined cycle intervals by use of the gas sensor element, the sensor output value S(n) decreasing as concentration of the specific gas increases, where n is an integer representing the chronological order of each sensor output value in a time series of sensor output values; third base-value calculation means for calculating a base value B(n) at the predetermined cycle intervals during a period in which a low-concentration signal is being generated, the base value B(n) being calculated in accordance with Expression (5):

$$B(n)=B(n-1)+k5[S(n)-B(n-1)]-k6[S(n)-S(n-t)] \quad (5)$$

where k5 and k6 are fifth and sixth coefficients, 0<k5<1, K6>0, and t is a positive integer; differential-value calculation means for calculating a difference value D(n) in accordance with Expression (6):

$$D(n)=B(n)-S(n) \quad (6)$$

on the basis of the sensor output value S(n) and the base value B(n); and high-concentration-signal generation means for generating a high-concentration signal when the difference value D(n) is greater than a high-concentration threshold Tu.

First, the base value B(n) will be described. The term B(n-1)+k5[S(n)-B(n-1)] of Expression (5) is a tracking term which changes more slowly than does the sensor output value S(n), while tracking the sensor output value S(n). This tracking term has characteristics such that when the value of the coefficient k5 is changed, the speed of tracking or following the sensor output value S(n) (i.e., sensitivity) changes. When the coefficient k5 increases (approaches 1), the tracking term follows the sensor output value S(n) more quickly with higher sensitivity. By contrast, when the coefficient k5 decreases (approaches 0), the rate of change of the value of the tracking term decreases, so that the value of the tracking term follows the sensor output value S(n) slowly. Meanwhile, the term -k6[S(n)-S(n-t)] is a decrease-emphasizing term for calculating a derivative. For example, when the present sensor output value S(n) decreases from the $t^{th}$ past sensor output value S(n−t); i.e., in the case where S(n)<S(n−t), the base value B(n) becomes greater than a virtual base value which is calculated by use of the above-described tracking term only without use of the decrease-emphasizing term.

In the gas detection apparatus of the present invention, the acquisition means is configured in such a manner that the sensor output value S(n) decreases as concentration of the specific gas increases. In the gas detection apparatus, the third base-value calculation means calculates the base value B(n) during a period in which the low-concentration signal is being generated. Further, the differential-value calculation means calculates a difference value D(n); and the high-concentration-signal generation means generates a high-concentration signal in place of the low-concentration signal when the difference value D(n) is greater than a high-concentration threshold Tu; i.e., in the case where D(n)=B(n)−S(n)>Tu. Specifically, during a period in which the low-concentration signal is being generated, the third base-value calculation means calculates a new base value B(n) by use of the above-described Expression (5).

As described above, when the sensor output value S(n) decreases, the virtual base value which is calculated by use of the tracking term only without use of the decrease-emphasizing term changes more slowly than does the sensor output value S(n), while tracking the sensor output value S(n). Meanwhile, the base value B(n) calculated by use of Expression (5) including the decrease-emphasizing term becomes greater than the virtual base value. Accordingly, the difference value D(n) calculated by use of Expression (6) becomes greater than a virtual difference value representing the difference between the sensor output value and the virtual base value. As a result, as compared with the virtual difference value, the difference value D(n) is more apt to exceed the high-concentration threshold Tu. In other words, a decrease in the sensor output value resulting from an increase in the gas concentration can be detected quickly to thereby generate the high-concentration signal. Further, in Expression (5), as described above, the value calculated by means of the tracking term changes more slowly than does the sensor output value S(n), while following the sensor output value S(n). Therefore, there can be prevented the situation where the gas concentration is erroneously detected to have increased by the influence of drift such as change in temperature or humidity, to thereby enable reliable gas detection.

The present invention according to claim 22 is a gas detection apparatus using a gas sensor element whose electrical characteristics change in accordance with concentration of a specific gas, comprising: acquisition means for acquiring a sensor output value S(n) at predetermined cycle intervals by use of the gas sensor element, the sensor output value S(n) decreasing as concentration of the specific gas increases, where n is an integer representing the chronological order of each sensor output value in a time series of sensor output values; third base-value calculation means for calculating a base value B(n) at the predetermined cycle intervals during a period in which a low-concentration signal is being generated, wherein when the sensor output value S(n) is smaller than a preceding base value B(n−1) representing a base value calculated in a preceding cycle, the third base-value calculation means calculates the base value B(n) in accordance with Expression (5):

$$B(n)=B(n-1)+k5[S(n)-B(n-1)]-k6[S(n)-S(n-t)] \quad (5)$$

where k5 and k6 are fifth and sixth coefficients, 0<k5<1, K6>0, and t is a positive integer, and when the sensor output value S(n) is greater than the preceding base value B(n−1), the third base-value calculation means calculates the base value B(n) in accordance with Expression (7):

$$B(n)=S(n) \quad (7)$$

differential-value calculation means for calculating a difference value D(n) in accordance with Expression (6):

$$D(n)=B(n)-S(n) \quad (6)$$

on the basis of the sensor output value S(n) and the base value B(n); and high-concentration-signal generation means for generating a high-concentration signal when the difference value D(n) is greater than a high-concentration threshold Tu.

The characteristics of the base value obtained by use of Expression (5) has already been described. In the gas detection apparatus of the present invention, the acquisition means is configured in such a manner that the sensor output value S(n) decreases as concentration of the specific gas increases. In the gas detection apparatus, the third base-value calculation means calculates the base value B(n) during a period in which the low-concentration signal is being generated. Further, the differential-value calculation means calculates a difference value D(n); and the high-concentration-signal generation means generates a high-concentration signal in place of the low-concentration signal when the difference value D(n) is greater than a high-concentration threshold Tu; i.e., in the case where D(n)=B(n)−S(n)>Tu. Specifically, during a period in which the low-concentration signal is being generated, the third base-value calculation means calculates a new base value B(n) by use of Expression (1) when a newly acquired sensor output value S(n) is greater than a preceding base value B(n−1).

As described above, when the sensor output value S(n) decreases, the virtual base value which is calculated by use of Expression (5) with the third term (the decrease-emphasizing term) deleted; i.e., the value calculated by use of the first term and the second term (tracking term) only, changes more slowly than does the sensor output value S(n), while tracking the sensor output value S(n). Meanwhile, the base value B(n) calculated by use of Expression (5) including the decrease-emphasizing term becomes greater than the virtual base value. Accordingly, the difference value D(n) calculated by use of Expression (6) becomes greater than a virtual difference value representing the difference between the virtual base value and the sensor output value. As a result, as compared with the virtual difference value, the difference value D(n) is more apt to exceed the high-concentration threshold Tu. In other words, a drop in the sensor output value resulting from an increase in the gas concentration can be detected quickly to thereby generate the high-concentration signal.

Further, in Expression (5), as described above, the value calculated by means of the tracking term changes more slowly than does the sensor output value S(n), while following the sensor output value S(n). Therefore, there can be prevented the situation where the gas concentration is erroneously detected to have increased by the influence of drift such as change in temperature or humidity, to thereby enable reliable gas detection.

Meanwhile, when the sensor output value S(n) is greater than the preceding base value B(n−1), the third base-value calculation means calculates the base value B(n) by use of Expression (7). In other words, the present sensor output value S(n) is used as the base value B(n). Through this operation, the newly calculated base value B(n) is forcibly made equal to the sensor output value S(n), irrespective of the magnitude of the preceding base value B(n−1).

Therefore, when the sensor output value S(n) becomes greater than the preceding sensor output value S(n−1) in the next cycle (after passage of the predetermined cycle interval), the relation S(n)>B(n−1) (=S(n−1)) is satisfied, and therefore the present sensor output value S(n) is used as the base value B(n). Therefore, during a period in which the relation of the sensor output value S(n) being grater than the preceding sensor output value S(n−1) continues, the sensor output value S(n) is equal to the base value B(n). That is, the base value B(n) changes to assume the same magnitude as that of the sensor output value S(n).

Therefore, at the point in time when the gas concentration starts to increase and the sensor output value becomes smaller than the preceding value; i.e., when the relation S(n)<S(n−1)) (=B(n−1) is satisfied, the sensor output value S(n) becomes smaller than the preceding base value B(n−1), and therefore, the calculation of the base value B(n) by use of Expression (5) is started. Accordingly, a positive difference (Dn) is generated between the base value B(n) and the sensor output value S(n); and when the difference (Dn) becomes greater than the high-concentration threshold Tu, so that the high-concentration signal is generated in place of the low-concentration signal. As described above, an increase in the gas concentration can be detected quickly, irrespective of changes in the base value B(n) in the past; i.e., irrespective of changes in the gas concentration in the past.

The gas detection apparatus according to claim 21 or 22 preferably comprises: fourth base-value calculation means for calculating a base value B(n) in accordance with Expression (8) at the predetermined cycle intervals during a period in which the high-concentration signal is being generated:

$$B(n)=B(n-1)+k7[S(n)-B(n-1)]-k8[S(n)-S(n-u)] \qquad (8)$$

where k7 and k8 are seventh and eighth coefficients, 0<k7<1, K8>0, and u is a positive integer; and low-concentration-signal generation means for generating a low-concentration signal when the difference value D(n) is smaller than a low-concentration threshold Td.

In the gas detection apparatus, the fourth base-value calculation means calculates the base value by use of Expression (8) during a period in which the high-concentration signal is being generated. The base value calculated by use of Expression (8) has the same characteristics as do those of the base value calculated by use of Expression (5). That is, the term B(n−1)+k7[S(n)−B(n−1)] of Expression (8) is a second tracking term which changes more slowly than does the sensor output value S(n) while following the sensor output value S(n).

Meanwhile, the term −k8[S(n)−S(n−u)] is a second decrease-emphasizing term for calculating a derivative. When the present sensor output value S(n) decreases from the $u^{th}$ past sensor output value S(n−u); i.e., in the case where S(n)<S(n−u), the base value B(n) becomes greater than a virtual base value which is calculated by use of the above-described second tracking term only and without use of the second increase-emphasizing term. Further, when the sensor output value increases after the decrease and the present sensor output value S(n) becomes smaller than the $u^{th}$ past sensor output value S(n−u); i.e., in the case where S(n)>S(n−u), the second decrease-emphasizing term produces a negative value. As a result, as compared with the virtual base value, the base value B(n) approaches the sensor output value S(n) more quickly.

During a period in which the high-concentration signal is being generated, the gas detection apparatus of the present invention calculates such a base value B(n) by use of the second base-value calculation means. Further, the low-concentration-signal generation means generates the low-concentration signal in place of the high-concentration signal when the difference value D(n) is smaller than the low-concentration threshold Td; i.e., in the case where D(n)=B(n)−S(n)<Td. Specifically, during a period in which the high-concentration signal is being generated, the fourth base-value calculation means calculates a new base value B(n) by use of the above-described Expression (8).

As described above, when the sensor output value S(n) decreases, the virtual base value which is calculated by use of Expression (8) with the second decrease-emphasizing term omitted; i.e., the value calculated by use of the second tracking term only, changes more slowly than does the sensor output value S(n), while tracking the sensor output value S(n). Meanwhile, the base value B(n) calculated by use of Expression (8) including the second decrease-emphasizing term becomes greater than the virtual base value. Accordingly, during a period in which the gas concentration increases after the low-concentration signal is switched to the high-concentration signal, whereby the sensor output value S(n) drops, the base value B(n) becomes greater than the virtual base value, by virtue of the presence of the second decrease-emphasizing term in Expression (8). Therefore, when the sensor output value rises temporarily in response to noise during a period in which the gas concentration is high, the difference value D(n) does not become smaller than the low-concentration threshold Td, whereby an erroneous operation of generating the low-concentration signal can be prevented.

Meanwhile, when the sensor output value rises in response to a decrease in the gas concentration, as described above, the base value B(n) approaches the sensor output value S(n) quickly. As a result, the difference value D(n) becomes smaller than the low-concentration threshold Td, and thus the decrease in the gas concentration can be detected quickly to thereby generate the low-concentration signal.

Preferably, the $t^{th}$ past sensor output value S(n−t) used in the decrease-emphasizing term is used in the second decrease-emphasizing term as the $u^{th}$ past sensor output value S(n−u); i.e., u=t. This can reduce the number of past sensor output values to be stored and reduce the program load through use of a common expression. Further, abrupt change in the base value can be avoided, which change would otherwise occur when the cycle number of the past sensor output value used in the calculation changes upon switching between the high-concentration signal and the low-concentration signal.

Preferably, the gas detection apparatus according to any one of claims 1 to 24 is incorporated in an automatic ventilation system for a vehicle. In the automatic ventilation system for a vehicle of the present invention, since a high-concentration signal and a low-concentration signal are generated properly in accordance with change in concentration of a specific gas, ventilation operation can be performed properly by use of the high-concentration signal and the low-concentration signal.

Preferably, the automatic ventilation system for a vehicle comprises an outside air introduction port; the gas detection apparatus according to any one of claims 1 to 24; and open-close instruction means for fully opening an open-close unit provided at the outside air introduction port when the low-concentration signal is generated and for fully closing the open-close unit of the outside air introduction port when the high-concentration signal is generated.

In the automatic ventilation system for a vehicle of the present invention, the above-described gas detection apparatus generates the low-concentration signal and the high-concentration signal in accordance with concentration of a specific signal; and the open-close instruction means outputs an open-close instruction signal so as to fully open the open-close unit of the outside air introduction port when the low-concentration signal is generated and so as to fully close the open-close unit of the outside air introduction port when the high-concentration signal is generated. Therefore, the open-close unit provided at the outside air introduction port can be driven properly in accordance with the concentration of the specific gas.

It is to be understood that both the foregoing general description and the following detailed description of the present invention are exemplary and explanatory, and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention.

DESCRIPTION OF THE PREFERRED EMBODIMENTS

Figure 1:
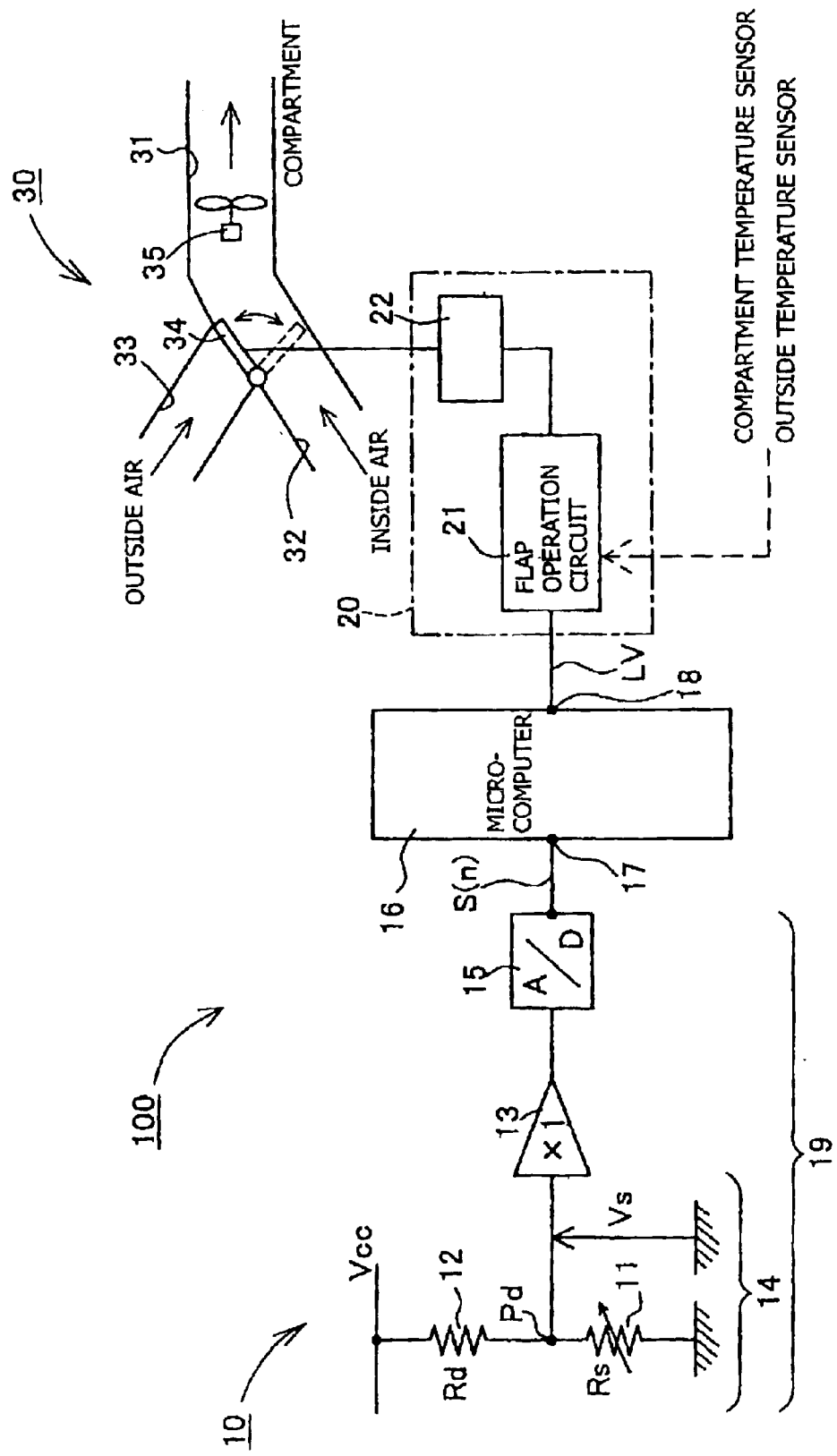
FIG. 1 is an explanatory view for schematically showing the gas detection apparatus and the vehicle automatic ventilation system according to a first embodiment of the invention.

A first embodiment of the present invention will now be described with reference to FIGS. 1 through 4. FIG. 1 includes a circuit diagram and a block diagram of a gas detection apparatus 10 according to the first embodiment, and a schematic representation of the structure of a vehicle automatic ventilation system 100 incorporating the gas detection apparatus 10. The system 100 includes the gas detection apparatus 10, which outputs a concentration signal LV in accordance with the concentration of a specific gas; a ventilation system 30, in which a flap 34 is rotated to thereby connect a duct 31 to either a duct 32 for introducing inside air or a duct 33 for introducing outside air; and an electronic control assembly 20 for controlling the flap 34 of the ventilation system 30 in accordance with the concentration signal LV.

The gas detection apparatus 10 will now be described. The gas detection apparatus 10 includes a gas sensor element 11 formed of an oxide semiconductor. The gas sensor element 11 responds to an oxidative gas component such as $NO_x$ contained in a measurement gas (specifically, air in the present embodiment), and the resistance Rs of the sensor element 11 increases in response to an increase in the concentration of the oxidative gas component. The gas sensor element 11 is provided in an automobile, outside the compartment thereof.

A sensor output value S(n) is obtained by means of the gas sensor element 11 and a sensor output acquisition circuit 19 including a sensor resistance conversion circuit 14, a buffer 13, and an A/D conversion circuit 15. The sensor resistance conversion circuit 14 outputs a sensor output electric potential Vs corresponding to the resistance Rs of the gas sensor element 11. Specifically, the sensor output electric potential Vs at a node Pd, which is obtained by dividing a power supply voltage Vcc by means of the gas sensor element 11 and a detection resistor 12 having a resistance of Rd, is output via the buffer 13. Therefore, in the sensor resistance conversion circuit 14, the resistance Rs and hence the sensor output electric potential Vs increase in accordance with an increase in the concentration of an oxidative gas such as $NO_x$.

A signal output from the buffer 13 (the sensor output electric potential Vs) is input to the A/D conversion circuit 15, and at predetermined cycle intervals the A/D conversion circuit 15 converts the signal to a digital sensor output value S(n). The sensor output value S(n) is output from the A/D conversion circuit 15 and then input to an input terminal 17 of a microcomputer 16. Reference letter "n" denotes an integer for expressing chronological order.

The concentration signal LV (high-concentration signal or low-concentration signal) for controlling the electronic control assembly 20 is output from an output terminal 18 of the microcomputer 16. The electronic control assembly 20 controls the flap 34 of the ventilation system 30 for controlling recirculation of air inside the automobile and introduction of outside air. Specifically, the electronic control assembly 20 controls the flap 34 such that, in terms of air flow, the inside air introduction duct 32 or the outside air introduction duct 33 is connected to the duct 31, which is connected to the compartment of the automobile.

A flap operation circuit 21 of the electronic control assembly 20 operates an actuator 22 in accordance with the concentration signal LV output from the output terminal 18 of the microcomputer 16, the concentration signal LV showing whether the concentration of an oxidative gas component (e.g., $NO_x$) increases or decreases, to thereby rotate the flap 34 such that the inside air introduction duct 32 or the outside air introduction duct 33 is connected to the duct 31.

Figure 2:
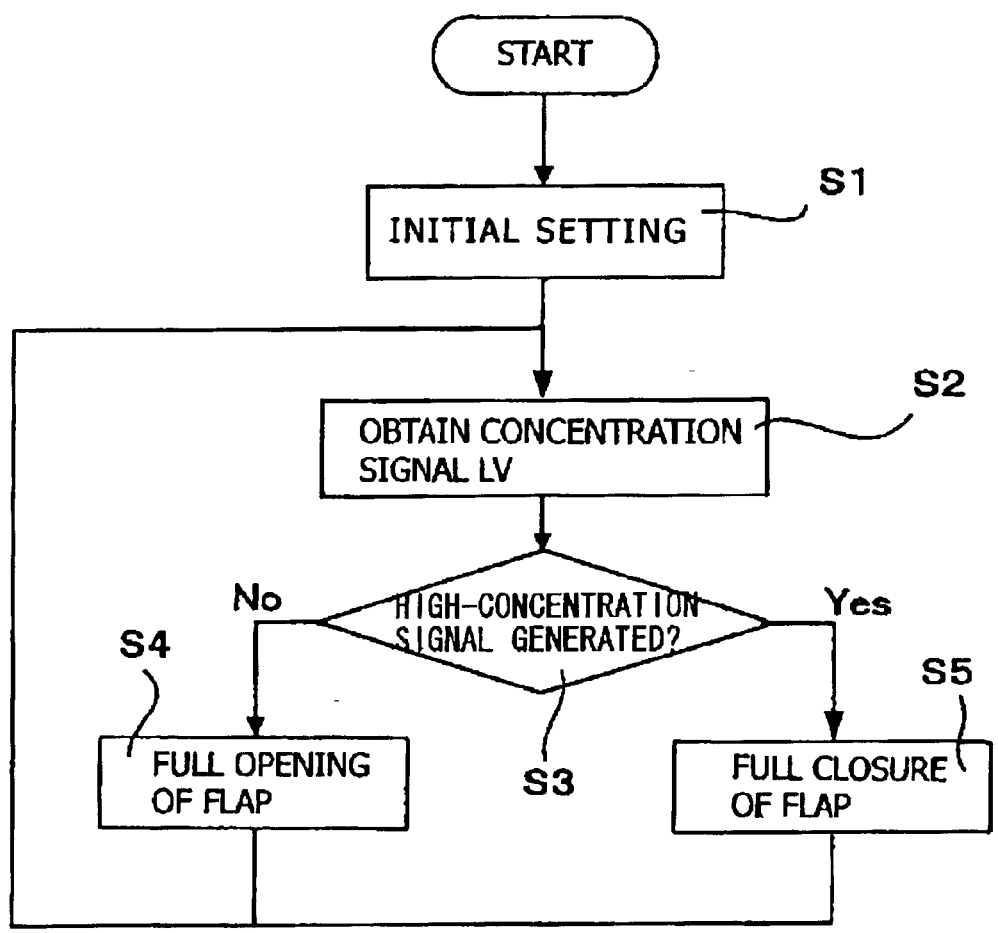
FIG. 2 is a flowchart for showing operation of vehicle automatic ventilation systems according to the first and second embodiments and the first and second modifications.

As shown in the flowchart of FIG. 2, after initial setting in step S1, in step S2 the concentration signal LV is obtained, and in step S3 a determination is made as to whether or not the level of the concentration signal LV is high; i.e., whether or not a high-concentration signal is being generated. In the case where the result of determination is "No"; i.e., in the case where a low-concentration signal is being generated, the concentration of a specific gas under measurement is low. Therefore, in step S4 full opening of the flap 34 is instructed. As a result, the flap 34 is rotated so as to connect the outside air introduction duct 33 to the duct 31, thereby introducing outside air into the compartment of the automobile. Meanwhile, in the case where the result of determination is "Yes" in step S3; i.e., in the case where a high-concentration signal is being generated, the concentration of the specific gas is high. Therefore, in step S5 full closure of the flap 34 is instructed. As a result, the flap 34 is rotated so as to connect the inside air introduction duct 32 to the duct 31, thereby stopping introduction of outside air and recirculating the air inside the compartment of the automobile.

A fan 35 for feeding air under pressure is provided in the duct 31. The flap operation circuit 21 is configured so as to rotate the flap 34 in accordance with merely the concentration signal LV; however, the flap operation circuit 21 may be configured such that the flap 34 is rotated by means of a microcomputer, on the basis of not only the concentration signal LV output from the gas detection apparatus 10 but also data obtained from, for example, a compartment temperature sensor, a humidity sensor, or an outside temperature sensor (see a broken line in FIG. 1).

In the microcomputer 16, the sensor output value $S(n)$ input through the input terminal 17 is processed in accordance with the below-described processing flow, to thereby detect change in the concentration of an oxidative gas component on the basis of change in the resistance Rs of the gas sensor element 11. Although not illustrated in detail in FIG. 1, the microcomputer 16, which has a known configuration, includes a microprocessor for performing operations, RAM for temporarily storing programs and data, and ROM for storing programs and data. The microcomputer 16 may incorporate the buffer 13 and the A/D conversion circuit 15.

Operation of the microcomputer 16 will next be described with reference to a flowchart of FIG. 3. When the engine of the automobile is started, the present control system starts. After the gas sensor element 11 is activated, in step S11 the microcomputer 16 performs initial setting. The microcomputer 16 stores, as a base value $B(0)$, a sensor output value $S(0)$ at a point in time when the gas sensor element 11 is activated ($B(0) = S(0)$). Furthermore, the microcomputer 16 generates a concentration signal LV of low level as a low-concentration signal.

Thereafter, the microcomputer 16 proceeds to step S12, so as to sequentially read a sensor signal; i.e., a present sensor output value $S(n)$ obtained through A/D conversion of the sensor output electric potential Vs at predetermined cycle intervals. Subsequently, in step S13, the microcomputer 16 determines whether or not the level of the concentration signal LV is high; i.e., whether or not there is generated a high-concentration signal for showing that the concentration of a specific gas (an oxidative gas in the present embodiment) is high. In the case where the result of determination is "No"; i.e., in the case where the concentration of the specific gas is low and the level of the concentration signal LV is low (i.e., a low-concentration signal is generated), the microcomputer 16 proceeds to step S14. In contrast, in the case where the result of determination is "Yes"; i.e., in the case where the concentration of the specific gas is high and the level of the concentration signal LV is high (i.e., a high-concentration signal is generated), the microcomputer 16 proceeds to step S17.

The case where a low-concentration signal is being generated; i.e., the case where the microcomputer proceeds to step S14, will now be described. In step S14, the microcomputer 16 determines whether or not the present sensor output value $S(n)$ is equal to or greater than the preceding base value $B(n-1)$. In the case where the result of determination is "Yes"; i.e., in the case where $S(n) > B(n-1)$, the microcomputer 16 proceeds to step S15. In contrast, in the case where the result of determination is "No"; i.e., in the case where $S(n) < B(n-1)$, the microcomputer 16 proceeds to step S16.

In step S15, the microcomputer 16 calculates a present base value $B(n)$ from the preceding base value $B(n-1)$, the present sensor output value $S(n)$, and a sensor output value $S(n-5)$ obtained 5 cycle intervals before the present (hereinafter called a "fifth past sensor output value") by use of the following Expression (1): $B(n) = B(n-1) + k1[S(n) - B(n-1)] - k2[S(n) - S(n-q)]$ (wherein the first coefficient k1 satisfies the relation: $0 < k1 < 1$, the second coefficient k2 satisfies the relation: $k2 > 0$, and q denotes a positive integer ($q = 5$ in the present embodiment)). Subsequently, the microcomputer 16 proceeds to step S18.

As described above, the term $B(n-1) + k1[S(n) - B(n-1)]$ (reference term) of Expression (1) consists of a tracking term. When the coefficient k1 satisfies the relation $0 < k1 < 1$, the value calculated by use of the tracking term changes to follow the present sensor output value $S(n)$, and the thus-calculated value changes more slowly than does the present sensor output value $S(n)$. Meanwhile, the term $-k2[S(n) - S(n-5)]$ is used to calculate the difference between the present sensor output value $S(n)$ and the fifth-past sensor output value $S(n-5)$, and serves as an increase-emphasizing term for emphasizing an increase in the sensor output. When the sensor output value increases (i.e., when $S(n) > S(n-5)$), the present base value $B(n)$ calculated by use of Expression (1) becomes smaller than the virtual present base value (hereinafter referred to as "$KB(n)$") calculated by use of solely the tracking term and without use of the increase-emphasizing term ($B(n) < KB(n)$).

Here, there will be considered the case where the virtual present base value $KB(n)$ is employed unlike the present first embodiment. Since the virtual present base value $KB(n)$ calculated by use of solely the tracking term follows the present sensor output value $S(n)$ with a delay, a difference is produced between $S(n)$ and $KB(n)$. This characteristic enables detection of an increase in the concentration of the specific gas. Specifically, in the below-described step S18, in place of the present difference value $D(n)$, the microcomputer 16 employs a virtual present difference value (hereinafter referred to as $KD(n)$) representing the difference between the present sensor output value $S(n)$ and the virtual present base value $KB(n)$. Use of the virtual present difference value enables detection of an increase in the concentration of the specific gas. That is, an increase in the concentration of the specific gas can be detected when the present control system is designed such that a high-concentration signal is generated when the virtual present difference value $KD(n)$ is greater than a positive high-concentration threshold Tu.

In the present embodiment, instead of the virtual base value $KB(n)$, the present base value $B(n)$ calculated by use of Expression (1) is used. Therefore, the present base value $B(n)$ becomes smaller than the virtual present base value KB(n), for the following reason. Since Expression (1) includes the increase-emphasizing term, when the sensor output value increases; i.e., when S(n) becomes greater than S(n−5), the value which is k2 times the increase is subtracted from the value of the tracking term. That is, when the sensor output value continues to increase, in each cycle, the present base value B(n) becomes smaller than the virtual present base value KB(n) by the value which is k2 times the increase in the sensor output. This difference between the present base value B(n) and the virtual present base value KB(n) accumulates. Therefore, the present difference value D(n) calculated in the below-described step S18 increases more quickly than does the virtual present difference value KD(n). That is, an increase in the sensor output value is emphasized by means of the increase-emphasizing term of Expression (1). Thus, when Expression (1) including the increase-emphasizing term is employed, an increase in the concentration of the specific gas can be detected more quickly as compared with the case where the virtual present base value KB(n) is used.

When the sensor output value gradually increases as a result of drift of the resistance Rs of the gas sensor element 11 attributed to change in temperature or humidity, the value calculated by the increase-emphasizing term of Expression (1) is very small. Therefore, contribution of the increase-emphasizing term to the calculated present base value B(n) becomes small, and the tracking term provides a relatively large contribution to the base value B(n). The tracking term changes to follow the sensor output value S(n), which gradually increases as a result of such drift. Therefore, when the sensor output value S(n) involves only a slow change such as drift, the present base value B(n) changes to follow the sensor output value S(n) substantially completely. Thus, the difference between the sensor output value S(n) and the base present value B(n), which is calculated in the below-described step S18, does not become large, thereby avoiding erroneous detection attributed to such drift.

In the case where the result of determination in step S14 is "No," the microcomputer 16 proceeds to step S16, employs the present sensor output value S(n) as the present base value B(n) (B(n)=S(n)), and proceeds to step S18. That is, when the present sensor output value S(n) is smaller than the preceding base value B(n−1), the present sensor output value S(n) is employed as the present base value B(n), for the following reasons.

If steps S14 and S16 are not provided, when the sensor output value S(n) decreases as a result of, for example, lowering of the concentration of the gas (S(n)<S(n−1)), the value of the increase-emphasizing term of Expression (1) becomes positive, and thus the present base value B(n) calculated by use of Expression (1) approaches the sensor output value S(n). Therefore, when the sensor output value continues to decrease, there arises a reverse state in which the present base value B(n) becomes greater than the present sensor output value S(n)(S(n)<B(n)). As a result, the difference between B(n) and S(n) (the present difference value D(n)), which is calculated in the below-described step S18, may become negative. When the gas concentration starts to increase and hence the sensor output value S(n) starts to increase during such a reverse state period, in the below-described step S20, a certain period of time elapses until the difference value D(n) exceeds the positive high-concentration threshold Tu, possibly delaying detection of an increase in the gas concentration.

In contrast, in the present embodiment, steps S14 and S16 are provided such that the present sensor output value S(n) is employed as the present base value B(n) in step S16. In this case, the present base value B(n) is made equal to the present sensor output value S(n), so that no reverse state arises. So long as the sensor output value continues to decrease with passage of time, and the relation S(n)<B(n−1)=S(n−1) is maintained, the present sensor output value S(n) is employed as the present base value B(n) in step S16.

Therefore, when the gas concentration starts to increase after the decrease and the sensor output value S(n) starts to increase after the decrease, S(n) becomes equal to or greater than B(n−1). Therefore, the microcomputer 16 produces a result "Yes" in step S14, and in step S15 calculates the present base value B(n) by use of Expression (1). The present base value B(n) is calculated on the basis of the preceding base value B(n−1); i.e., the preceding sensor output value S(n−1). The thus-calculated present base value B(n) is smaller than the virtual present base value KB(n) which slowly changes to follow the sensor output value S(n). That is, the relation S(n)>KB(n)>B(n) is satisfied. When the sensor output value S(n) continues to increase, the relation S(n)>B(n−1) is maintained. Therefore, when the concentration of the specific gas increases, the difference value D(n) representing the difference between the present base value B(n) and the present sensor output value S(n) quickly becomes large as compared with the case where steps S14 and S16 are not provided or the case where the increase-emphasizing term of Expression (1) is not provided. Thus, an increase in the concentration of the specific gas can be detected more quickly.

Subsequent to step 515 or S16, in step S18 the microcomputer 16 calculates the difference value D(n) by use of Expression (2): D(n)=S(n)−B(n), and in step S20 compares the difference value D(n) with the high-concentration threshold Tu (Tu>0). In the case where the result of determination in step S20 is "Yes"; i.e., in the case where D(n)>Tu, the microcomputer 16 proceeds to step S22. In contrast, in the case where the result of determination in step S20 is "No"; i.e., in the case where D(n)≦Tu, the microcomputer 16 proceeds to step S24 while skipping step S22. The high-concentration threshold Tu used in step S20 is a threshold for determining whether or not the concentration of the specific gas is high.

As described below, in order to prevent chattering, the high-concentration threshold Tu is set to be greater than a low-concentration threshold Td employed in step S21. However, Tu may be set equal to Td, to thereby consolidate steps S18 and S19, and steps S20 and S21. In the case where the result of determination in step S20 is "Yes"; i.e., in the case where D(n)>Tu, the difference value D(n) representing the difference between the present sensor output value S(n) and the present base value B(n) calculated by use of Expression (1) in step S15 is large. In this case, conceivably, the sensor output value S(n) has increased in response to an increase in the concentration of the specific gas (oxidative gas), and hence the difference between the sensor output value (Sn) and the base value B(n) has increased. Subsequently, the microcomputer 16 proceeds to step S22, and generates a high-concentration signal; specifically, the concentration signal LV of high level. Thereafter, the microcomputer 16 proceeds to step S24.

In contrast, when the result of determination in step S20 is "No"; i.e., in the case where D(n)≦Tu, the difference value D(n) representing the difference between the present sensor output value S(n) and the present base value B(n) calculated by use of Expression (1) in step S15 is small. In this case, conceivably, the concentration of the specific gas (oxidative gas) is maintained at a low level. Therefore, the microcomputer 16 skips step S22 in order to maintain the concentration signal LV of low level (low-concentration signal), and then proceeds to step S24. Thereafter, in step S24, the microcomputer 16 stores the present base value B(n) calculated in step S15 or S16. After the microcomputer 16 waits for elapse of the cycle time of A/D sampling operation in step S25, the microcomputer 16 returns to step S12 so as to obtain a sensor output value S(n).

Next will be described the case where a high-concentration signal is being generated; i.e., the case where the microcomputer 16 produces a result of determination "Yes" in step S13 and proceeds to step S17. In step S17, the microcomputer 16 calculates a present base value B(n) from the preceding base value B(n−1) and the present sensor output value S(n) by use of an expression similar to that employed in step S15; i.e., the following Expression (4): B(n)=B(n−1)+k3[S(n)−B(n−1)]−k4[S(n)−S(n−r)] (wherein the third coefficient k3 satisfies the relation 0<k3<k1<1, the fourth coefficient k4 satisfies the relation k4>0, and r denotes a positive integer (r=5 in the present embodiment)). Subsequently, the microcomputer proceeds to step S19.

Similar to the case of the aforementioned Expression (1), the term B(n−1)+k3[S(n)−B(n−1)] (second reference term) of Expression (4) consists of a second tracking term. When the coefficient k3 satisfies the relation 0<k3<1, the value calculated by use of the second tracking term changes to follow the present sensor output value S(n), and the thus-calculated value changes more slowly than does the present sensor output value S(n). Meanwhile, the term −k4[S(n)−S(n−5)] is used to calculate the difference between the present sensor output value S(n) and the fifth-past sensor output value S(n−5) as in the case of the increase-emphasizing term of Expression (1). This term serves as a second increase-emphasizing term for emphasizing an increase in the sensor output. When the sensor output value increases (S(n)>S(n−5)), the present base value B(n) calculated by use of Expression (4) becomes smaller than the virtual present base value KB(n) calculated by use of solely the second tracking term and without use of the second increase-emphasizing term. When the sensor output value is assumed to have an increase period in which the sensor output value increases and a decrease period which is subsequent to the increase period and in which sensor output value decreases, in the decrease period, the value which is k4 times the decrease (negative increase) is added to the present base value B(n) by the second increase-emphasizing term. Therefore, the rate of change in the base value B(n) becomes greater than that in the virtual base value KB(n) calculated by use of solely the second tracking term. Thus, during the decrease period, the base value B(n) approaches the sensor output value S(n) more quickly than does the virtual base value KB(n).

Therefore, in the case where the microcomputer 16 produces a result of determination "Yes" in step S13 after generating a high-concentration signal in step S22, and then calculates the present base value B(n) by use of Expression (4) in step S17, when the sensor output value S(n) increases in response to an increase in the gas concentration, the present base value B(n) becomes smaller than the virtual present base value KB(n). As a result, the difference between the sensor output value S(n) and the present base value B(n) becomes greater than the difference between the sensor output value S(n) and the virtual present base value KB(n). Therefore, unlike the case where the virtual present base value KB(n) is employed, there can be prevented erroneous detection which would otherwise occur when the sensor output value S(n) temporarily decreases in response to noise in a state in which the gas concentration is high. Such erroneous determination occurs in such a manner that the difference value D(n) calculated in the below-described step S19 becomes smaller, and in step S21, the microcomputer 16 erroneously determines that the difference value D(n) is equal to or smaller than the low-concentration threshold Td (D(n)≦Td).

When the sensor output value S(n) decreases in response to a decrease in the gas concentration, the base value B(n) quickly approaches the sensor output value S(n) as described above. Therefore, the difference value D(n) becomes smaller than the low-concentration threshold Td, and a decrease in the gas concentration can be detected quickly, to thereby generate a low-concentration signal. Thus, while avoiding erroneous determination regarding concentration decrease, a decrease in the gas concentration can be detected quickly.

As described above, the value calculated by use of solely the second tracking term of Expression (4) changes to follow the present sensor output value S(n), and the thus-calculated value changes more slowly than does the present sensor output value S(n). Therefore, in the case where the present base value B(n) calculated by use of Expression (4) including the first and second terms is employed, even when, while the gas concentration decreases, the sensor output value insufficiently decreases as a result of drift or adsorption, the high-concentration signal is prevented from being maintained, and a decrease in the gas concentration can be detected reliably, whereby the high-concentration signal can be switched to a low-concentration signal.

Subsequent to step S17, in step S19 the microcomputer 16 calculates the difference value D(n) by use of Expression (2): D(n)=S(n)−B(n), and in step S21 compares the difference value D(n) with the low-concentration threshold Td (Td≧0). In the case where the result of determination in step S21 is "Yes"; i.e., in the case where D(n)≦Td, the microcomputer 16 proceeds to step S23. Meanwhile, in the case where the result of determination in step S21 is "No"; i.e., in the case where D(n)>Td, the microcomputer 16 proceeds to step S24 while skipping step S23. The low-concentration threshold Td used in step S21 is a threshold for determining whether or not the concentration of the specific gas is low.

The low-concentration threshold Td is smaller than the high-concentration threshold Tu employed in step S20 (Tu>Td). These two thresholds; i.e., the high-concentration threshold Tu and the low-concentration threshold Td, are employed in order to provide hysteresis characteristics and to prevent chattering which would otherwise occur during the course of switching between the low-concentration signal and the high-concentration signal.

In the case where the result of determination in step S21 is "Yes"; i.e., in the case where D(n)≦Td, the difference value D(n) representing the difference between the present sensor output value S(n) and the present base value B(n) calculated by use of Expression (4) in step S17 is small. In this case, conceivably, the sensor output value S(n) has decreased in response to a decrease in the concentration of the specific gas (oxidative gas), and thus the difference between the sensor output value (Sn) and the base value B(n) has decreased. Therefore, the microcomputer 16 proceeds to step S23, and generates a low-concentration signal; specifically, the concentration signal LV of low level. Thereafter, the microcomputer 16 proceeds to step S24.

In contrast, when the result of determination in step S21 is "No"; i.e., in the case where D(n)>Td, the difference value D(n) representing the difference between the present sensor output value S(n) and the present base value B(n) calculated by use of Expression (4) in step S17 is large. In this case, conceivably, the concentration of the specific gas is maintained at a high level. Therefore, the microcomputer 16 skips step S23 in order to maintain the concentration signal LV of high level (high-concentration signal), and then proceeds to step S24.

Thereafter, in step S24, the microcomputer 16 stores the present base value B(n) calculated in step S17. After the microcomputer 16 waits for elapse of the cycle time of A/D sampling operation in step S25, the microcomputer 16 returns to step S12 so as to obtain a sensor output value S(n).

As described above, in the first embodiment, an increase in the gas concentration can be detected quickly during a period in which the low-concentration signal is being generated. Also, a decrease in the gas concentration can be detected quickly during a period in which the high-concentration signal is being generated, while avoiding erroneous determination regarding concentration decrease.

In the first embodiment, the sensor output acquisition circuit 19 corresponds to the acquisition means; steps S15 and S16 correspond to the first calculation means and the first base value calculation means; step S17 corresponds to the second calculation means and the second base value calculation means; step S22 corresponds to the high-concentration signal generation means; and step S23 corresponds to the low-concentration signal generation means. The circuit and steps are mere examples of these means.

In the first embodiment, subsequent to step S16, the microcomputer 16 proceeds to step S18. In the case where the relation B(n)=S(n) is established in step S16, in step S18 the difference value D(n) necessarily becomes zero. Since the high-concentration threshold Tu is positive (Tu>0), the microcomputer 16 necessarily produces a result of determination "No" in step S20, and proceeds to step S24, while skipping step S22 in order to maintain the generation of the low-concentration signal. Therefore, as shown by a broken line in FIG. 3, the microcomputer 16 may proceed directly from step S16 to step S24 while skipping steps S18, S20, and S22, since the generation of the low-concentration signal can be continued.

Figure 3:
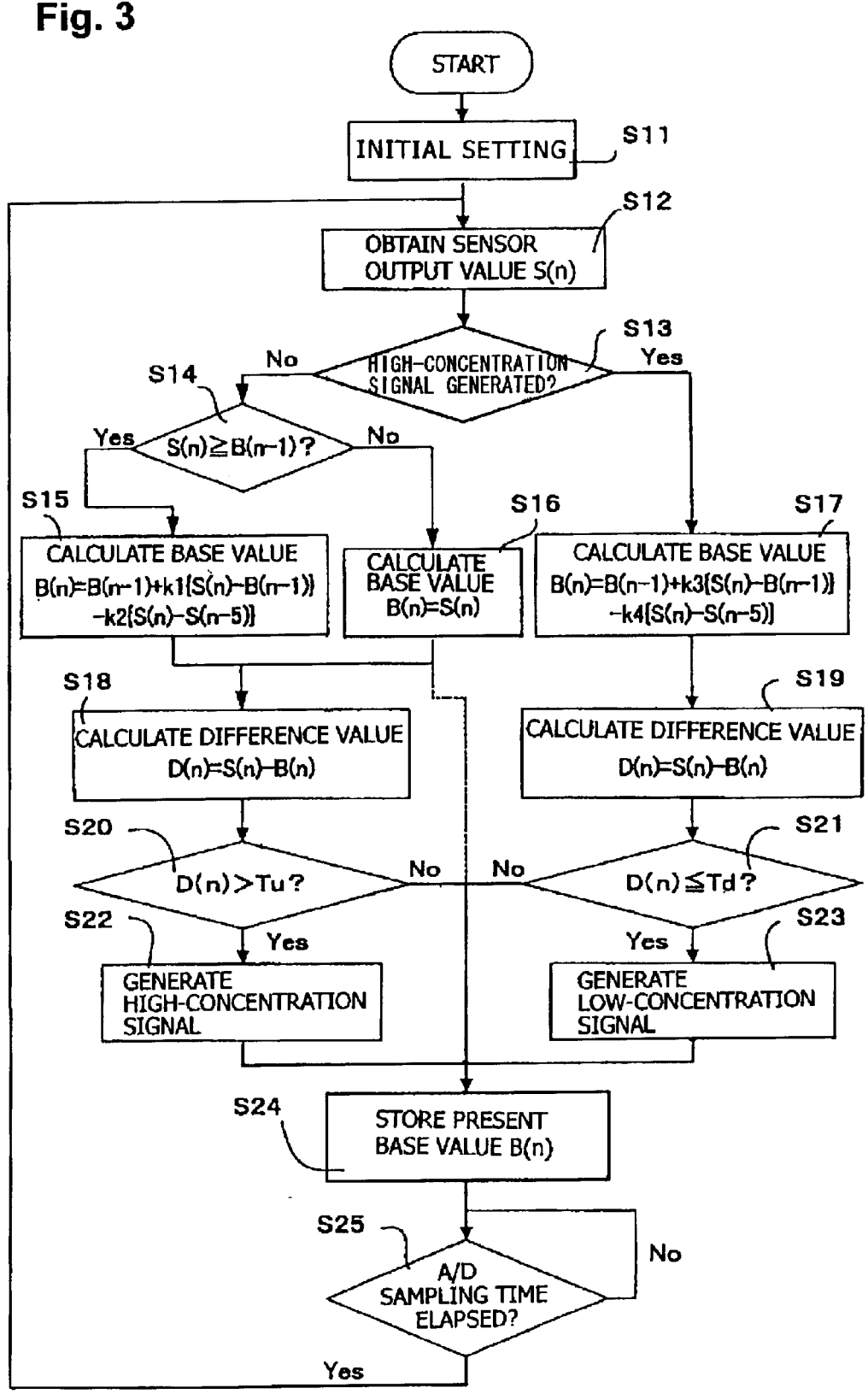
FIG. 3 is a flowchart for showing operation of the microcomputer incorporated in the gas detection apparatus according to the first embodiment.
Figure 4:
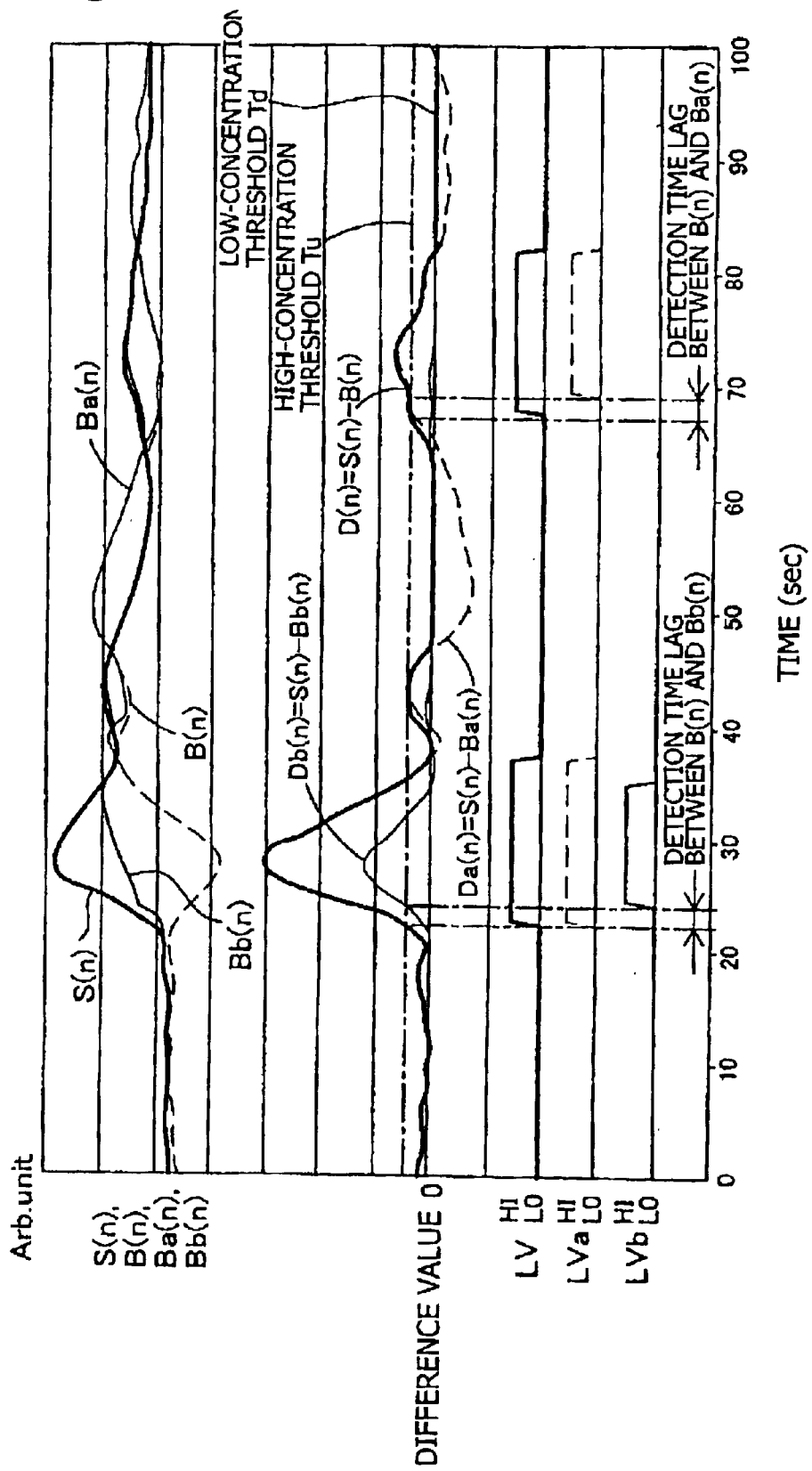
FIG. 4 is a graph relating to the first embodiment and showing changes in the base value B(n), the difference value D(n), and the concentration signal LV for changes in the sensor output value S(n), for comparison with changes in the base value Ba(n), the difference value Da(n), and the concentration signal LVa, which are obtained through the processing of FIG. 3 with steps S14 and S16 removed, as well as changes in the base value Bb(n), the difference value Db(n), and the concentration signal LVb, which are obtained through the processing of FIG. 3 with the third term (increase-emphasizing term, or second increase-emphasizing term) removed from the expressions used in steps S15 and S17.

FIG. 4 shows a sensor output value S(n) which was actually measured, as well as a base value B(n), a difference value D(n), and a concentration signal LV, which were calculated through operation in accordance with the flowchart shown in FIG. 3. For comparison, FIG. 4 also shows data of a modified example; specifically, a base value Ba(n), a difference value Da(n), and a concentration signal LVa, which were calculated, by use of the above-measured sensor output value S(n), through operation in accordance with a flowchart which was modified through removal of steps S14 and S16 from the flowchart shown in FIG. 3. FIG. 4 also shows data of a comparative example; specifically, a base value Bb(n), a difference value Db(n), and a concentration signal LVb, which were calculated through operation in accordance with the flowchart shown in FIG. 3, except that an expression obtained through removal of the third term (increase-emphasizing term) from Expression (1) was employed in step S15, and that an expression obtained through removal of the third term (second increase-emphasizing term) from Expression (4) was employed in step S17.

In the present embodiment, when a low-concentration signal is being generated, the base value B(n) shown by a broken line of FIG. 4 is calculated by use of Expression (1): B(n)=B(n−1)+k1[S(n)−B(n−1)]−k2[S(n)−S(n−5)] in the case where S(n)≧B(n−1), or by use of the expression B(n)=S(n) in the case where S(n)<B(n−1). Meanwhile, when a high-concentration signal is being generated, the base value B(n) is calculated by use of Expression (4): B(n)=B(n−1)+k3[S(n)−B(n−1)]−k4[S(n)−S(n−5)]. In Expressions (1) and (4), k1 is 1/10, k2 is 1/2, k3 is 1/32, and k4 is 1/5.

In the modified example shown in FIG. 4, when a low-concentration signal is being generated, regardless of the magnitudes of S(n) and Ba(n−1), the base value Ba(n) shown by a thin line in FIG. 4 is calculated by use of the following expression: Ba(n)=Ba(n−1)+k1[S(n)−Ba(n−1)]−k2[S(n)−S(n−5)]. Meanwhile, when a high-concentration signal is being generated, the base value Ba(n) is calculated by use of the following expression: Ba(n)=Ba(n−1)+k3[S(n)−Ba(n−1)]−k4[S(n)−S(n−5)]. In the above expressions, k1 is 1/10, k2 is 1/2, k3 is 1/32, and k4 is 1/5.

In the comparative example shown in FIG. 4, when a low-concentration signal is being generated, the base value Bb(n) shown by a solid line in FIG. 4 is calculated by use of the following expression: Bb(n)=Bb(n−1)+k1[S(n)−Bb(n−1)] in the case where S(n)≧Bb(n−1), or by use of the expression Bb(n)=S(n) in the case where S(n)<Bb(n−1). Meanwhile, when a high-concentration signal is being generated, the base value Bb(n) is calculated by use of the expression Bb(n)=Bb(n−1)+k3[S(n)−Bb(n−1)]. In the above expressions, k1 is 1/10, and k3 is 1/32.

When the concentration of $NO_x$ changes, the sensor output value S(n) changes. The base value B(n) is calculated on the basis of the thus-changed sensor output value S(n). Until 22 seconds have elapsed, the base value B(n) is almost equal to the sensor output value S(n). When the sensor output value S(n) drastically increases after elapse of 22 seconds, the base value B(n) decreases. The base value Ba(n) calculated in the modified example changes in a manner similar to that of the base value B(n). The base value B(n) and the base value Ba(n) change in the above-described manners, since each of the base values is calculated by use of the expression including the increase-emphasizing term. Meanwhile, the base value Bb(n) calculated in the comparative example gradually increases so as to follow the sensor output value S(n), since the base value Bb(n) is calculated by use of the expression consisting of the tracking term, which changes to follow the sensor output value S(n). Therefore, the difference value D(n) calculated by use of the expression D(n)=S(n)−B(n) and the difference value Da(n) calculated by use of the expression Da(n)=S(n)−Ba(n) drastically increase, but the difference value Db(n) calculated by use of the expression: Db(n)=S(n)−Bb(n) becomes smaller than D(n) or Da(n), and the difference value Db(n) increases at a rising speed lower than that of D(n) or Da(n). When the difference value D(n), Da(n), or Db(n) exceeds the high-concentration threshold Tu, the level of the concentration signal LV, LVa, or LVb is switched from L-level to H-level.

Comparison among the concentration signal LV for the present embodiment, the concentration signal LVa for the modified example, and the concentration signal LVb for the comparative example reveals the difference in rising speed among the difference values D(n), Da(n), and Db(n). Specifically, as shown in FIG. 4, the level of the concentration signal LV or LVa is switched from L-level to H-level after elapse of about 22 seconds, whereas the level of the concentration signal LVb is switched from L-level to H-level after elapse of 24 seconds. Thus, according to the present embodiment or the modified example, an increase in the concentration of a specific gas can be detected more quickly as compared with the case of the comparative example in which the base value Bb(n) is calculated by use of the expression including no increase-emphasizing term.

After about 30 seconds have elapsed, the sensor output value S(n) decreases. Conceivably, the concentration of $NO_x$ has decreased. In the present embodiment or the modified example, the level of the concentration signal LV or LVa is switched to L-level after elapse of about 37 seconds. In the comparative example, the level of the concentration signal LVb is switched to L-level after elapse of about 35 seconds. Until the elapse of about 67 seconds, the levels of the concentration signals LV, LVa, and LVb are maintained at L-level. However, in the modified example, the difference value Da(n) becomes negative after elapse of about 47 to about 65 seconds, since calculation of the base value Ba(n) is continued even in the case where S(n)<B(n−1), unlike the case of the present embodiment in which S(n) is employed as B(n) in the case where S(n)<B(n−1).

Therefore, when the sensor output value S(n) somewhat increases in response to an increase in the concentration of $NO_x$ after elapse of about 65 seconds, in the case of the present embodiment, the increase in the $NO_x$ concentration is detected and the level of the concentration signal LV is switched to H-level after elapse of about 67 seconds. Meanwhile, in the case of the modified example, the increase in the $NO_x$ concentration is detected and the level of the concentration signal LVa is switched to H-level after elapse of about 69 seconds. The results show that, in the present embodiment wherein the relation S(n)=B(n) is forcibly established in the case where S(n)<B(n−1), when the $NO_x$ concentration increases again, the increase in the $NO_x$ concentration is detected more quickly as compared with the case of the modified example.

In the comparative example, the level of the concentration signal LVb is maintained at L-level after elapse of 67 seconds; i.e., an increase in the $NO_x$ concentration is not detected. The results show that, in the present embodiment or the modified example, in which the base value B(n) or Ba(n) is calculated by use of the expression including the increase-emphasizing term, change in the gas concentration is detected more reliably as compared with the case of the comparative example in which the expression including no increase-emphasizing term is employed.

Figure 5:
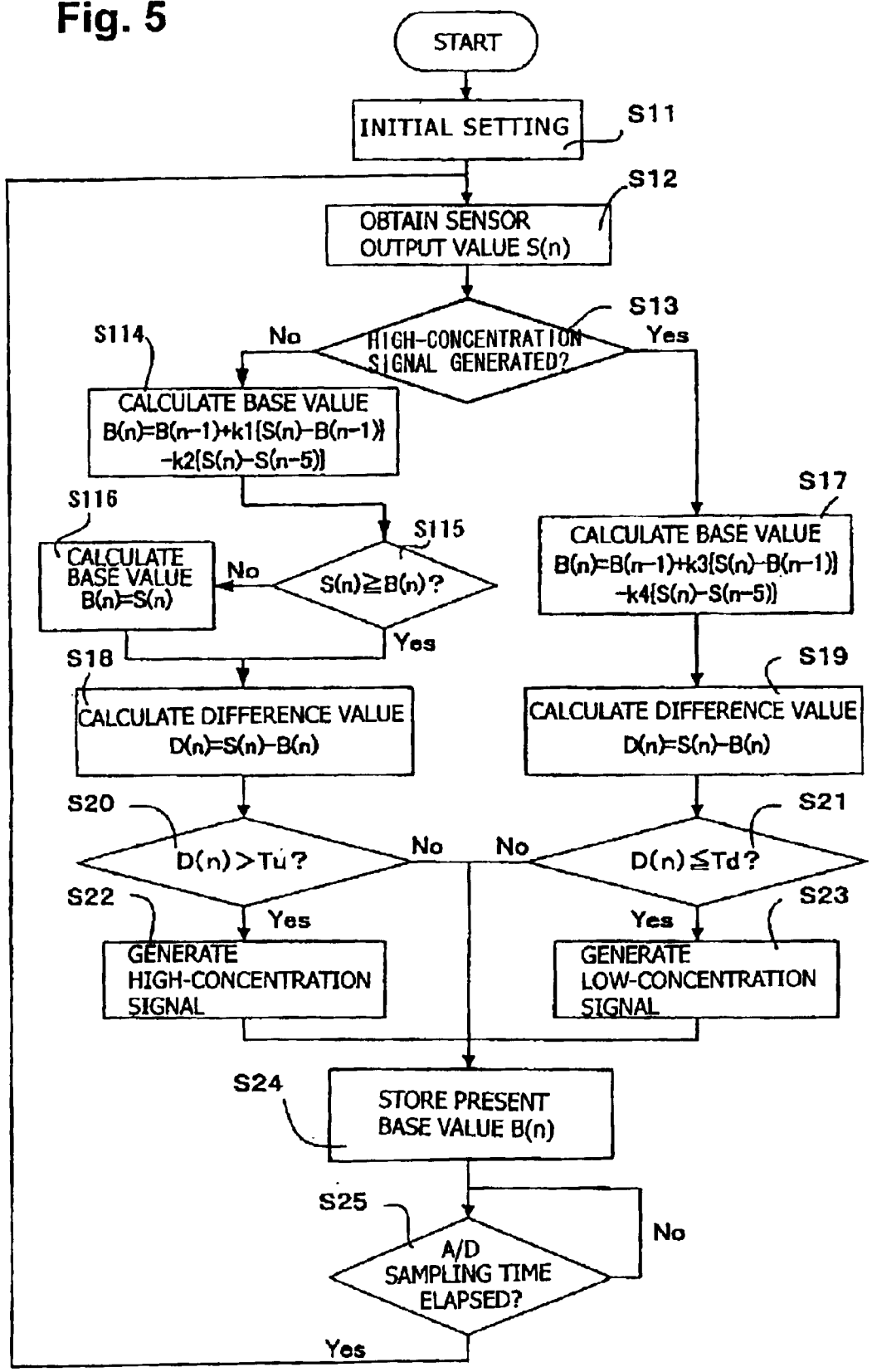
FIG. 5 is a flowchart for showing operation of the microcomputer incorporated in the gas detection apparatus according to the first modification.

A modification of the first embodiment will next be described with reference to FIG. 5. The vehicle automatic ventilation system 100 of the first modification includes the gas detection apparatus 10 described above in the first embodiment. That is, the system 100 is configured such that change in the concentration of an oxidative gas component (e.g., $NO_x$) is detected, and the flap 34 is opened and closed on the basis of the resultant data. Since the present modification slightly differs from the first embodiment in processing flow of the microcomputer 16, the different portion will be described mainly. The same portions are denoted by the same symbols or numerals, and their descriptions are omitted or simplified.

In the aforementioned first embodiment, when, in step S13, the microcomputer 16 yields a determination "No"; i.e., when the microcomputer determines that a low-concentration signal is being generated, in step S14, the microcomputer 16 determines whether or not S(n) is equal to or greater than B(n−1), and then calculates the base value B(n) in step S15 or step S16 (see FIG. 3). The processing flow of the microcomputer 16 of the present modification differs from that of the first embodiment in that steps S114, S115, and S116 are provided in place of the aforementioned steps S14, S15, and S16.

Specifically, when, in step S13, the microcomputer 16 yields a determination "No"; i.e., when the microcomputer determines that a low-concentration signal is being generated, in step S114, the microcomputer 16 calculates the present base value B(n) from the present sensor output value S(n) by use of Expression (1). Subsequently, in step S115, the microcomputer 16 compares the thus-calculated present base value B(n) with the present sensor output value S(n); specifically, the microcomputer determines whether or not S(n) is equal to or greater than B(n). In the case where the result of determination is "Yes"; i.e., in the case where the calculated present base value B(n) is equal to or smaller than the present sensor output value S(n), the microcomputer 16 proceeds to step S18, and calculates the difference value D(n) in a manner similar to that of the first embodiment.

Like the case of the present base value B(n) calculated in step S15 of the first embodiment, the present base value B(n) calculated by use of Expression (1) in step S114 becomes smaller by the value which is k2 times the increase in the sensor output value than the virtual present base value KB(n) calculated by use of merely the tracking term of Expression (1). Therefore, the present difference value D(n) calculated in step S18 increases more quickly than does the virtual difference value KD(n). That is, an increase in the sensor output value is emphasized by means of the increase-emphasizing term of Expression (1). Thus, in the first modification, through employment of Expression (1) having the increase-emphasizing term, the microcomputer 16 quickly yields a determination "Yes" in step S20 and detects an increase in the concentration of the specific gas more quickly.

In the case where "No" is yielded in step S115; i.e., in the case where the calculated present base value B(n) is greater than the present sensor output value S(n), the microcomputer 16 proceeds to step S116, and employs the present sensor output value S(n) as a new present base value B(n) instead of the present base value B(n) calculated in step S114. That is, when the present base value B(n) is greater than the present sensor output value S(n), the present sensor output value S(n) is employed as the present base value B(n). Thereafter, the microcomputer 16 proceeds to step S18, and calculates the difference value D(n) in a manner similar to that of the first embodiment.

As described above, in the first modification as well, an increase in the gas concentration can be detected quickly during a period in which the low-concentration signal is being generated. Also, a decrease in the gas concentration can be detected quickly during a period in which the high-concentration signal is being generated, while avoiding erroneous determination regarding concentration decrease. In the first modification, steps S114, S115, and S16 correspond to the first calculation means and the first base value calculation means. These steps are mere examples of these means.

A second embodiment of the present invention will next be described with reference to FIGS. 6 and 7. A gas detection apparatus 40 according to the second embodiment and a vehicle automatic ventilation system 140 incorporating the apparatus 40 somewhat differ, in structure and processing flow, from the gas detection apparatus 10 and the ventilation system 100 of the first embodiment. Specifically, the gas detection apparatus 10 of the first embodiment incorporates the gas sensor element 11 which responds to an oxidative gas component such as $NO_x$, wherein the resistance Rs of the sensor element 11 increases in response to an increase in the concentration of the oxidative gas component. Meanwhile, the gas detection apparatus 40 of the second embodiment incorporates a gas sensor element 41 which responds to a reducing gas component such as CO or HC, wherein the resistance Rs of the sensor element 41 decreases in response to an increase in the concentration of the reducing gas component. A sensor resistance conversion circuit 44 of the second embodiment outputs a sensor output electric potential Vs corresponding to the resistance Rs of the gas sensor element 41. In the sensor resistance conversion circuit 44, the resistance Rs decreases and the sensor output electric potential Vs decreases in response to an increase in the concentration of a reducing gas component such as CO or HC. Further, since the present modification slightly differs from the first embodiment in processing flow of the microcomputer 16, the different portion will be described mainly. The same portions are denoted by the same symbols or numerals, and their descriptions are omitted or simplified.

The gas detection apparatus 40 and the vehicle automatic ventilation system 140 will now be described with reference to FIG. 6. The gas detection apparatus 40 incorporates the gas sensor element 41 formed of an oxide semiconductor. As described above, the gas sensor element 41 responds to a reducing gas, and the resistance Rs of the sensor element 41 decreases in response to an increase in the concentration of the reducing gas. A sensor output value S(n) is obtained by means of the gas sensor element 41 and a sensor output acquisition circuit 49 including a sensor resistance conversion circuit 44, a buffer 13, and an A/D conversion circuit 15.

The sensor resistance conversion circuit 44 outputs a sensor output electric potential Vs corresponding to the resistance Rs of the gas sensor element 41. In the sensor resistance conversion circuit 44, the sensor output electric potential Vs at a node Pd decreases in accordance with an increase in the concentration of a reducing gas. In a manner similar to that of the first embodiment, the sensor output electric potential Vs output from the buffer 13 is input to the A/D conversion circuit 15, and converted to a digital sensor output value S(n) in the A/D conversion circuit 15 at predetermined sampling intervals. Subsequently, the sensor output value S(n) is input to an input terminal 17 of a microcomputer 16.

In a manner similar to that of the first embodiment, a concentration signal LV (high-concentration signal or low-concentration signal) for controlling an electronic control assembly 20 is output from an output terminal 18 of the microcomputer 16. The concentration signal LV shows the concentration of a reducing gas component. In accordance with, for example, the flowchart shown in FIG. 2, the electronic control assembly 20 controls a flap 34 of a ventilation system 30 for controlling recirculation of air inside the automobile and introduction of outside air. In the microcomputer 16, the sensor output value S(n) input through the input terminal 17 is processed in accordance with the below-described processing flow, to thereby detect change in the concentration of a reducing gas component on the basis of change in the resistance Rs of the gas sensor element 41.

Operation of the microcomputer 16 in the present embodiment 2 will next be described with reference to a flowchart of FIG. 7. When the engine of the automobile is started, the present control system starts. After the gas sensor element 41 is activated, in step S11 the microcomputer 16 performs initial setting in a manner similar to that of the first embodiment. Thereafter, the microcomputer 16 proceeds to step S12, so as to sequentially read a present sensor output value S(n). Subsequently, in step S13, the microcomputer 16 determines whether or not a high-concentration signal is being generated. In the case where the result of determination is "No"; i.e., in the case where a low-concentration signal is being generated, the microcomputer 16 proceeds to step S214. In contrast, in the case where the result of determination is "Yes"; i.e., in the case where a high-concentration signal is being generated, the microcomputer 16 proceeds to step S217.

The case where a low-concentration signal is being generated; i.e., the case where the microcomputer proceeds to step S214, will now be described. In step S214, unlike the case of the first embodiment, the microcomputer 16 determines whether or not the present sensor output value S(n) is equal to or smaller than the preceding base value B(n−1). This is because, contrary to the first embodiment, the present sensor output value S(n) decreases in response to an increase in the concentration of a specific gas (reducing gas). In the case where the result of determination is "Yes"; i.e., in the case where S(n)≦B(n−1), the microcomputer 16 proceeds to step S215. In contrast, in the case where the result of determination is "No"; i.e., in the case where S(n)>B(n−1), the microcomputer 16 proceeds to step S216.

In step S215, the microcomputer 16 calculates a present base value B(n) from the preceding base value B(n−1) and the present sensor output value S(n) by use of the following Expression (5): B(n)=B(n−1)+k5[S(n)−B(n−1)]−k6[S(n)−S(n−t)] (wherein the fifth coefficient k5 satisfies the relation: 0<k5<1, the sixth coefficient k6 satisfies the relation: k6>0, and t denotes a positive integer (t=5 in the present embodiment)). Subsequently, the microcomputer 16 proceeds to step S218.

As described above, the term B(n−1)+k5[S(n)−B(n−1)] (reference term) of Expression (5) consists of a tracking term. When the fifth coefficient k5 satisfies the relation 0<k5<1, the value calculated by use of the tracking term changes to follow the present sensor output value S(n), and the thus-calculated value changes more slowly than does the present sensor output value S(n). Meanwhile, the term −k6[S(n)−S(n−5)] is used to calculate the difference between the present sensor output value S(n) and the fifth-past sensor output value S(n−5), and serves as a decrease-emphasizing term for emphasizing a decrease in the sensor output. When the sensor output value decreases (i.e., when S(n)<S(n−5)), the present base value B(n) calculated by use of Expression (5) becomes greater than the virtual present base value KB(n) calculated by use of solely the tracking term and without use of the decrease-emphasizing term (B(n)>KB(n)).

Here, there will be considered the case where the virtual present base value KB(n) is employed unlike the present second embodiment. Since the virtual present base value KB(n) calculated by use of solely the tracking term follows the present sensor output value S(n) with a delay, a difference is produced between S(n) and KB(n). This characteristic enables detection of an increase in the concentration of the specific gas. Specifically, in the below-described step S218, in place of the present difference value D(n), the microcomputer 16 employs a virtual present difference value (hereinafter referred to as KD(n)) representing the difference between the present sensor output value S(n) and the virtual present base value KB(n). Use of the virtual present difference value enables detection of an increase in the concentration of the specific gas. That is, an increase in the concentration of the specific gas can be detected when the present control system is designed such that a high-concentration signal is being generated when the virtual present difference value KD(n) is greater than a positive high-concentration threshold Tu.

In the second embodiment, instead of the virtual present difference value KD(n), the present base value B(n) calculated by use of Expression (5) is used. Therefore, the present base value B(n) becomes greater than the virtual present base value KB(n), for the following reason. Since Expression (5) includes the decrease-emphasizing term, when the sensor output value decreases; i.e., when S(n) becomes smaller than S(n−5), the value which is k6 times the decrease is subtracted from the value of the tracking term. That is, when the sensor output value continues to decrease, in each cycle, the present base value B(n) becomes greater than the virtual present base value KB(n) by the value which is k6 times the decrease in the sensor output value. This difference between the present base value B(n) and the virtual present base value KB(n) accumulates. Therefore, the present difference value D(n) calculated in the below-described step S218 increases more quickly than does the virtual present difference value KD(n). That is, a decrease in the sensor output value is emphasized by means of the decrease-emphasizing term of Expression (5). Thus, through employment of Expression (5) including the decrease-emphasizing term, an increase in the concentration of the specific gas can be detected more quickly as compared with the case where the virtual present base value KB(n) is used.

When the sensor output value gradually decreases as a result of drift of the resistance Rs of the gas sensor element 41 attributed to change in temperature or humidity, the value calculated by the decrease-emphasizing term of Expression (5) is very small. Therefore, contribution of the decrease-emphasizing term to the calculated present base value B(n) becomes small, and the tracking term provides a relatively large contribution to the base value B(n). The tracking term changes to follow the sensor output value S(n), which gradually decreases as a result of such drift. Therefore, when the sensor output value S(n) involves only a slow change such as drift, the present base value B(n) changes to follow the sensor output value S(n) substantially completely. Thus, the difference between the sensor output value S(n) and the present base value B(n), which is calculated in the below-described step S218, does not become large, thereby avoiding erroneous detection attributed to such drift.

In the case where the result of determination in step S214 is "No," the microcomputer 16 proceeds to step S216, employs the present sensor output value S(n) as the present base value B(n) (B(n)=S(n)), and proceeds to step S218. That is, in step S214, when the present sensor output value S(n) is greater than the preceding base value B(n−1), the present sensor output value S(n) is employed as the present base value B(n), for the following reasons.

If steps S214 and S216 are not provided, when the sensor output value S(n) increases as a result of, for example, lowering of the concentration of the gas (S(n)>S(n−1)), the value of the third term (i.e., the decrease-emphasizing term) of Expression (5) becomes negative, and thus the present base value B(n) calculated by use of Expression (5) approaches the sensor output value S(n). Therefore, when the sensor output value continues to increase, there arises a reverse state in which the present base value B(n) becomes smaller than the present sensor output value S(n)(S(n)>B(n)). As a result, the difference between B(n) and S(n) (the present difference value D(n)), which is calculated in the below-described step S218, may become negative. When the gas concentration starts to increase and hence the sensor output value S(n) starts to decrease during such a reverse state, in the below-described step S20, a certain period of time elapses until the difference value D(n) exceeds the positive high-concentration threshold Tu, possibly delaying detection of an increase in the gas concentration.

In contrast, in the case of the second embodiment, steps S214 and S216 are provided such that the present sensor output value S(n) is employed as the present base value B(n) in step S216. In this case, the present base value B(n) is made equal to the present sensor output value S(n), so that no reverse state arises. So long as the sensor output value continues to increase with passage of time, and the relation S(n)>B(n−1)=S(n−1) is maintained, the present sensor output value S(n) is employed as the present base value B(n) in step S216.

Therefore, when the gas concentration starts to increases after the decrease and the sensor output value S(n) starts to decrease after the increase, S(n) becomes equal to or smaller than B(n−1). Therefore, the microcomputer 16 produces a result "Yes" in step S214, and in step S215 calculates the present base value B(n) by use of Expression (5). The present base value B(n) is calculated on the basis of the preceding base value B(n−1); i.e., the preceding sensor output value S(n−1). The thus-calculated present base value B(n) is greater than the virtual present base value KB(n) which slowly changes to follow the sensor output value S(n). That is, the relation S(n)<KB(n)<B(n) is satisfied. When the sensor output value S(n) continues to decrease, the relation S(n)<B(n−1) is maintained. Therefore, when the concentration of the specific gas increases, the difference value D(n) representing the difference between the present base value B(n) and the present sensor output value S(n) increases more quickly as compared with the case where steps S214 and S216 are not provided or the case where the third term (i.e., decrease-emphasizing term of Expression (5) is not provided. Thus, an increase in the concentration of the specific gas can be detected more quickly.

Subsequent to step S215 or S216, in step S218 the microcomputer 16 calculates the difference value D(n) by use of Expression (6): D(n)=B(n)−S(n), which differs from Expression (3) employed in the first embodiment.

Thereafter, in a manner similar to that of the first embodiment, in step S20 the microcomputer 16 compares the difference value D(n) with the high-concentration threshold Tu (Tu>0). In the case where the result of determination is "Yes," the microcomputer 16 proceeds to step S22. In contrast, in the case where the result of determination is "No," the microcomputer 16 proceeds to step S24.

In the case where the result of determination in step S20 is "Yes," the difference value D(n) representing the difference between the present sensor output value S(n) and the present base value B(n) calculated by use of Expression (5) in step S215 is large. In this case, conceivably, the sensor output value S(n) has decreased in response to an increase in the concentration of the specific gas (reducing gas), and thus the difference between the sensor output value (Sn) and the base value B(n) has increased. Subsequently, the microcomputer 16 proceeds to step S22, and generates a high-concentration signal; specifically, the concentration signal LV of high level. Thereafter, the microcomputer 16 proceeds to step S24.

In contrast, when the result of determination in step S20 is "No," the difference value D(n) is small. In this case, conceivably, the concentration of the specific gas (reducing gas) is maintained at a low level. Subsequently, the microcomputer 16 maintains the generation of the low-concentration signal; specifically, the concentration signal LV of low level, and proceeds to step S24.

Thereafter, in step S24, the microcomputer 16 stores the present base value B(n) calculated in step S215 or S216. After the microcomputer 16 waits for elapse of the cycle time of A/D sampling operation in step S25, the microcomputer 16 returns to step S12 so as to obtain a sensor output value S(n).

Next will be described the case where a high-concentration signal is being generated; i.e., the case where the microcomputer 16 produces a result of determination "Yes" in step S13 and proceeds to step S217. In step S217, the microcomputer 16 calculates a present base value B(n) from the preceding base value B(n−1) and the present sensor output value S(n) by use of an expression similar to that employed in step S215; i.e., the following Expression (8):
$B(n)=B(n-11)+k7[S(n)-B(n-1)]-k8[S(n)-S(n-u)]$
(wherein the seventh coefficient k7 satisfies the relation 0<k7≦k5<1, the eighth coefficient k8 satisfies the relation k8>0, and u denotes a positive integer (u=5 in the present embodiment)). Subsequently, the microcomputer proceeds to step S219.

Similar to the case of the aforementioned Expression (5), the term B(n−1)+k7[S(n)−B(n−1)] (second reference term) of Expression (8) consists of a second tracking term. When the coefficient k7 satisfies the relation 0<k7<1, the value calculated by use of the second tracking term changes to follow the present sensor output value S(n), and the thus-calculated value changes more slowly than does the present sensor output value S(n). Meanwhile, the term −k8[S(n)−S(n−5)] is used to calculate the difference between the present sensor output value S(n) and the fifth-past sensor output value S(n−5) as in the case of the decrease-emphasizing term of Expression (5). This term serves as a second decrease-emphasizing term for emphasizing a decrease in the sensor output. When the sensor output value decreases (S(n)<S(n−5)), the present base value B(n) calculated by use of Expression (8) becomes greater than the virtual present base value KB(n) calculated by use of solely the second tracking term and without use of the second decrease-emphasizing term. When the sensor output value is assumed to have a decrease period in which the sensor output value decreases and an increase period which is subsequent to the decrease period and in which sensor output value increases, in the increase period, the value which is k8 times the increase is subtracted from the present base value B(n) by the second decrease-emphasizing term. Therefore, the rate of change in the base value B(n) becomes smaller than that in the virtual base value KB(n) calculated by use of solely the second tracking term. Thus, during the increase period, the base value B(n) approaches the sensor output value S(n) more quickly than does the virtual base value KB(n).

Therefore, in the case where the microcomputer 16 produces a result of determination "Yes" in step S13 after generating a high-concentration signal in step S22, and then calculates the present base value B(n) by use of Expression (8) in step S217, when the sensor output value S(n) decreases in response to an increase in the gas concentration, the present base value B(n) becomes greater than the virtual present base value KB(n). As a result, the difference between the sensor output value S(n) and the present base value B(n) becomes greater than the difference between the sensor output value S(n) and the virtual present base value KB(n). Therefore, unlike the case where the virtual present base value KB(n) is employed, there can be prevented erroneous detection which would otherwise occur when the sensor output value S(n) temporarily increases in response to noise in a state in which the gas concentration is high. Such erroneous determination occurs in such a manner that the difference value D(n) calculated in the below-described step S219 becomes smaller, and in step S21, the microcomputer 16 erroneously determines that the difference value D(n) is equal to or smaller than the low-concentration threshold Td (D(n)≦Td).

When the sensor output value S(n) increases in response to a decrease in the gas concentration, the base value B(n) quickly approaches the sensor output value S(n) as described above. Therefore, the difference value D(n) becomes smaller than the low-concentration threshold Td, and a decrease in the gas concentration can be detected quickly, to thereby generate a low-concentration signal. Thus, while avoiding erroneous determination regarding concentration decrease, a decrease in the gas concentration can be detected quickly.

The value calculated by use of solely the second tracking term of Expression (8) changes to follow the present sensor output value S(n), and the thus-calculated value changes more slowly than does the present sensor output value S(n). Therefore, even when, while the gas concentration decreases, the sensor output value insufficiently increases as a result of drift or adsorption, the high-concentration signal is prevented from being maintained, and a decrease in the gas concentration can be detected reliably, whereby the high-concentration signal can be switched to a low-concentration signal.

Subsequent to step S217, in step S219 the microcomputer 16 calculates the difference value D(n) by use of Expression (6): D(n)=B(n)−S(n). Thereafter, as in the case of the first embodiment, in step S21 the microcomputer 16 compares the difference value D(n) with the low-concentration threshold Td (Td≧0). In the case where the result of determination in step S21 is "Yes," the microcomputer 16 proceeds to step S23. Meanwhile, in the case where the result of determination in step S21 is "No," the microcomputer 16 proceeds to step S24. The low-concentration threshold Td used in step S21 is a threshold for determining whether or not the concentration of the specific gas is low. As in the case of the first embodiment, in order to prevent chattering, the low-concentration threshold Td is set to be smaller than the high-concentration threshold Tu (Tu>Td).

In the case where the result of determination in step S21 is "Yes," the difference value D(n) calculated by use of Expression (6) in step S219 is small. In this case, conceivably, the concentration of the specific gas (reducing gas) has decreased, and hence the sensor output value S(n) has increased. Subsequently, the microcomputer 16 proceeds to step S23, and generates a low-concentration signal; specifically, the concentration signal LV of low level. Thereafter, the microcomputer 16 proceeds to step S24.

In contrast, when the result of determination in step S21 is "No," the difference value D(n) is large. In this case, conceivably, the concentration of the specific gas is maintained at a high level. Subsequently, the microcomputer 16 generates a high-concentration signal; specifically, the concentration signal LV of high level, and proceeds to step S24.

Thereafter, in step S24, the microcomputer 16 stores the present base value B(n) calculated in step S217. After the microcomputer 16 waits for elapse of the cycle time of A/D sampling operation in step S25, the microcomputer 16 returns to step S12 so as to obtain a sensor output value S(n).

As described above, in the second embodiment as well, an increase in the gas concentration can be detected quickly during a period in which a low-concentration signal is being generated. Also, a decrease in the gas concentration can be detected quickly during a period in which a high-concentration signal is being generated, while avoiding erroneous determination regarding concentration decreases.

In the second embodiment, the sensor output acquisition circuit 49 corresponds to the acquisition means; steps S215 and S216 correspond to the first calculation means and the third base value calculation means; step S217 corresponds to the second calculation means and the fourth base value calculation means; step S22 corresponds to the high-concentration signal generation means; and step S23 corresponds to the low-concentration signal generation means. The circuit and steps are mere examples of these means.

In the second embodiment, subsequent to step S216, the microcomputer 16 proceeds to step S218. In the case where the relation B(n)=S(n) is established in step S216, for the same reason as described above in the first embodiment, the microcomputer 16 maintains the generation of the low-concentration signal and proceeds to step S24. Therefore, as shown by a broken line in FIG. 7, the microcomputer 16 may proceed directly from step S216 to step S24.

Figure 8:
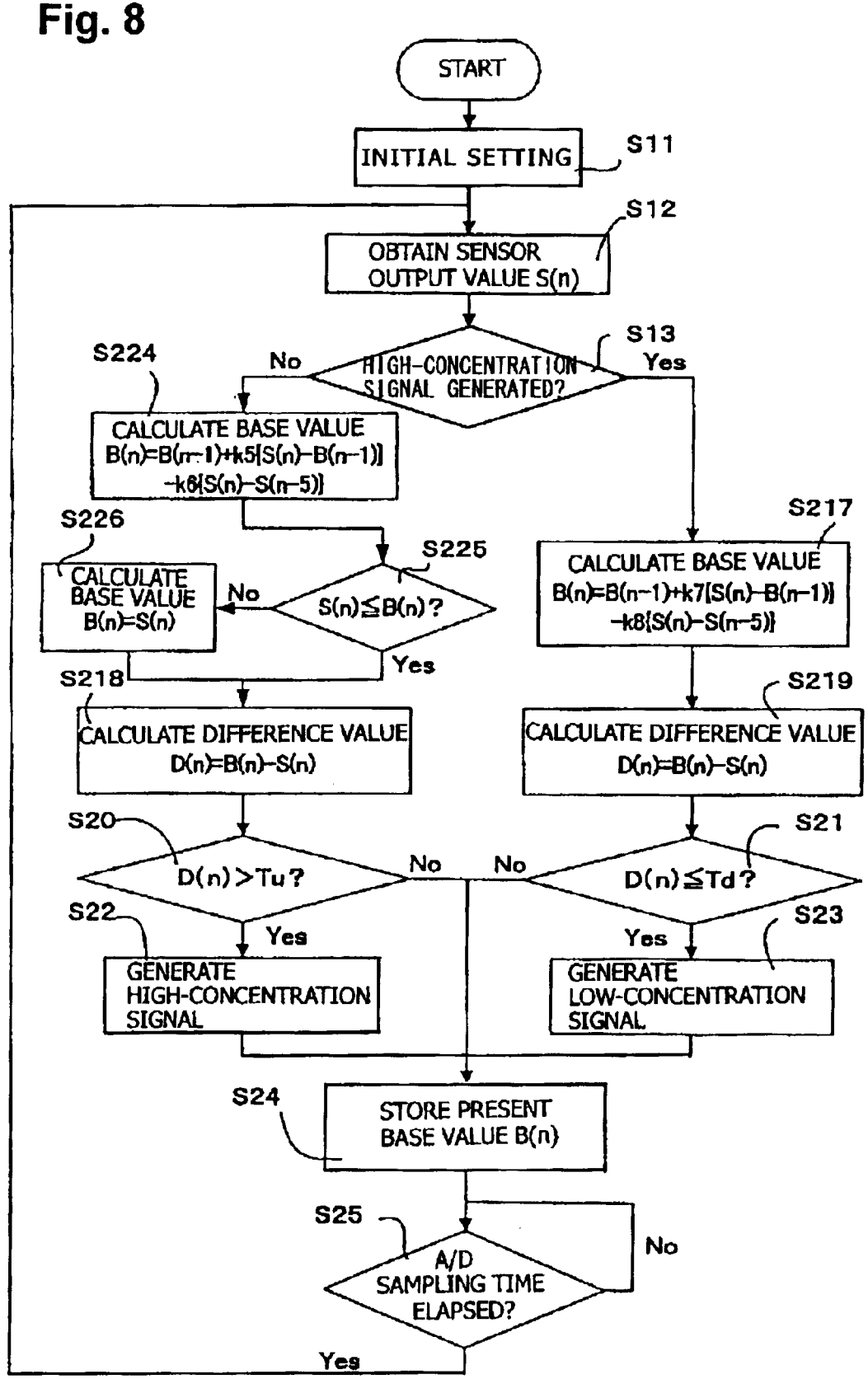
FIG. 8 is a flowchart for showing operation of the microcomputer incorporated in the gas detection apparatus according to the second modification.

A second modification of the second embodiment will next be described with reference to FIG. 8. The vehicle automatic ventilation system 140 of the second modification includes the gas detection apparatus 40 described above in the second embodiment. That is, the system 140 is configured such that change in the concentration of a reducing gas component (e.g., CO or HC) is detected, and the flap 34 is opened and closed on the basis of the resultant data. Since the present modification slightly differs from the second embodiment in processing flow of the microcomputer 16, the different portion will be described mainly. The same portions are denoted by the same symbols or numerals, and their descriptions are omitted or simplified.

Figure 7:
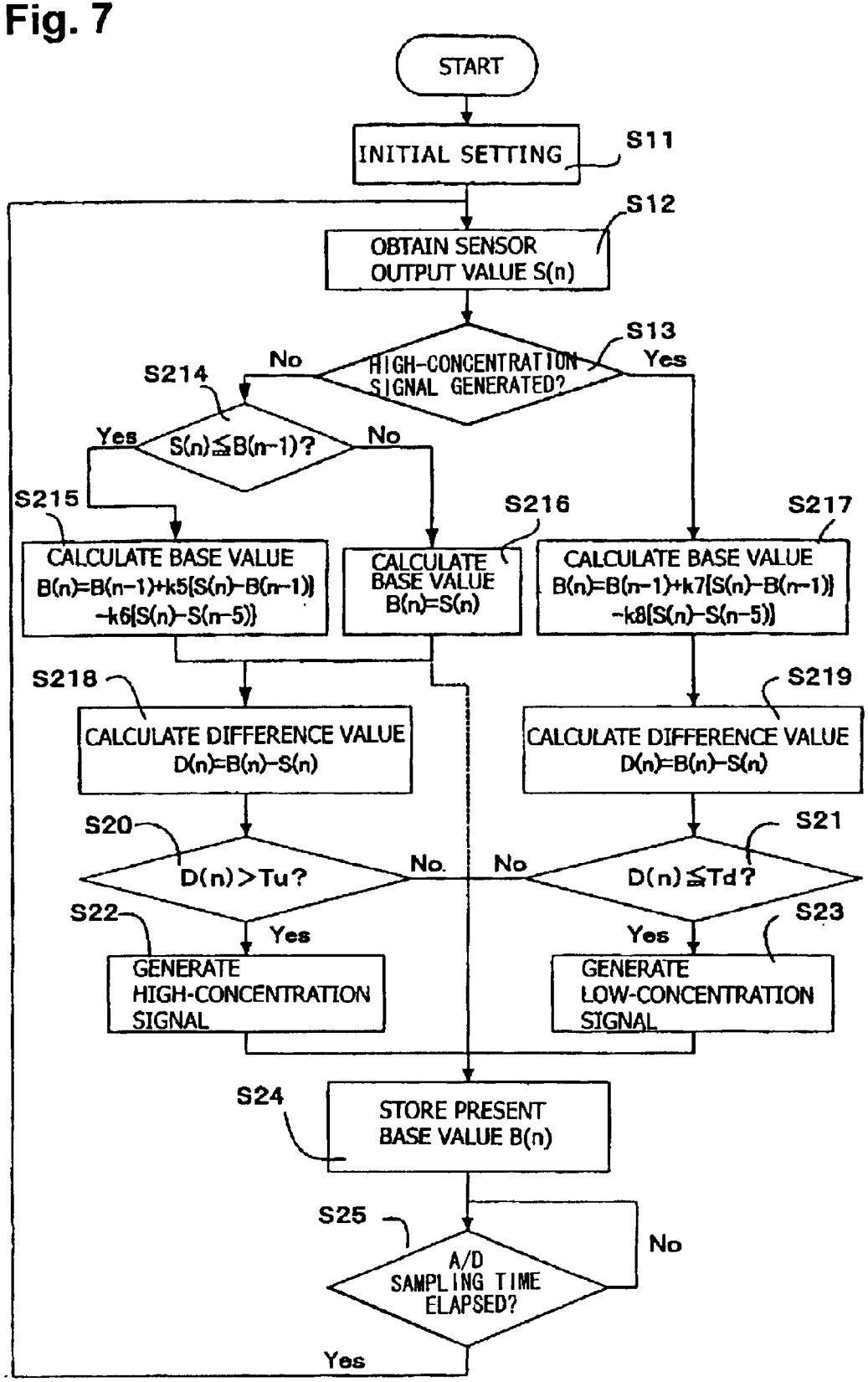
FIG. 7 is a flowchart for showing operation of the microcomputer incorporated in the gas detection apparatus according to the second embodiment.

In the aforementioned second embodiment, when, in step S13, the microcomputer 16 yields a determination "No"; i.e., when the microcomputer determines that a low-concentration signal is being generated, in step S214, the microcomputer 16 determines whether or not S(n) is equal to or smaller than B(n−1), and then calculates the base value B(n) in step S215 or step S216 (see FIG. 7). The processing flow of the microcomputer 16 of the present modification differs from that of the second embodiment in that steps S224, S225, and S226 are provided in place of the aforementioned steps S214, S215, and S216.

Specifically, when, in step S13, the microcomputer 16 yields a determination "No"; i.e., when the microcomputer 16 determines that a low-concentration signal is being generated, in step S224, the microcomputer 16 calculates the present base value B(n) from the present sensor output value S(n) by use of Expression (5). Subsequently, in step S225, the microcomputer 16 compares the thus-calculated present base value B(n) with the present sensor output value S(n); specifically, the microcomputer 16 determines whether or not S(n) is equal to or smaller than B(n). In the case where the result of determination is "Yes"; i.e., in the case where the calculated present base value B(n) is equal to or greater than the present sensor output value S(n), the microcomputer 16 proceeds to step S218, and calculates the difference value D(n) in a manner similar to that of the second embodiment.

Like the case of the present base value B(n) calculated in step S215 of the second embodiment, the present base value B(n) calculated by use of Expression (5) in step S224 becomes greater by the value which is k6 times the decrease in the sensor output value than the virtual present base value KB(n) calculated by use of solely the tracking term of Expression (5). Therefore, the present difference value D(n) calculated in step S218 increase more quickly than does the virtual difference value KD(n). That is, a decrease in the sensor output value is emphasized by means of the third term (i.e., the decrease-emphasizing term) of Expression (5). Thus, in the second modification as well, when Expression (5) including the decrease-emphasizing term is employed, the microcomputer 16 yields a determination "Yes" in step S20 and detects an increase in the concentration of the specific gas more quickly.

In contrast, in the case where the result of determination is "No" in step S225; i.e., in the case where S(n)>B(n), the microcomputer 16 proceeds to step S226, and employs the present sensor output value S(n) as a new present base value B(n) instead of the present base value B(n) calculated in step S224. That is, when the present sensor output value S(n) is greater than the present base value B(n), the present sensor output value S(n) is employed as the present base value B(n). Thereafter, the microcomputer 16 proceeds to step S218, and calculates the difference value D(n) in a manner similar to that of the second embodiment.

Thus, in the second modification as well, an increase in the gas concentration can be detected quickly during a period in which a low-concentration signal is being generated. Also, a decrease in the gas concentration can be detected quickly during a period in which a high-concentration signal is being generated, while avoiding erroneous determination regarding concentration decreases.

In the second modification, steps S224, S225, and S226 correspond to the first calculation means and the third base value calculation means. These steps are mere examples of these means.

Although the present invention has been described with reference to the first and second embodiments and the first and second modifications, the present invention is not limited to these embodiments and modifications, and various changes and modifications may be made without departing from the scope of the present invention.

Each of the aforementioned embodiments and modifications employs the gas detection apparatus 10 or 40 which outputs, via the buffer 13, the sensor output electric potential Vs at the node Pd, which is obtained by dividing the power supply voltage Vcc by means of the gas sensor element 11 or 41 and the detection resistor 12 having a resistance of Rd. However, no particular limitations are imposed on the sensor resistance conversion circuit, so long as it outputs a sensor output electric potential corresponding to the resistance Rs of the gas sensor element. Therefore, the sensor resistance conversion circuit may be a circuit other than the aforementioned voltage division circuit.

Figure 6:
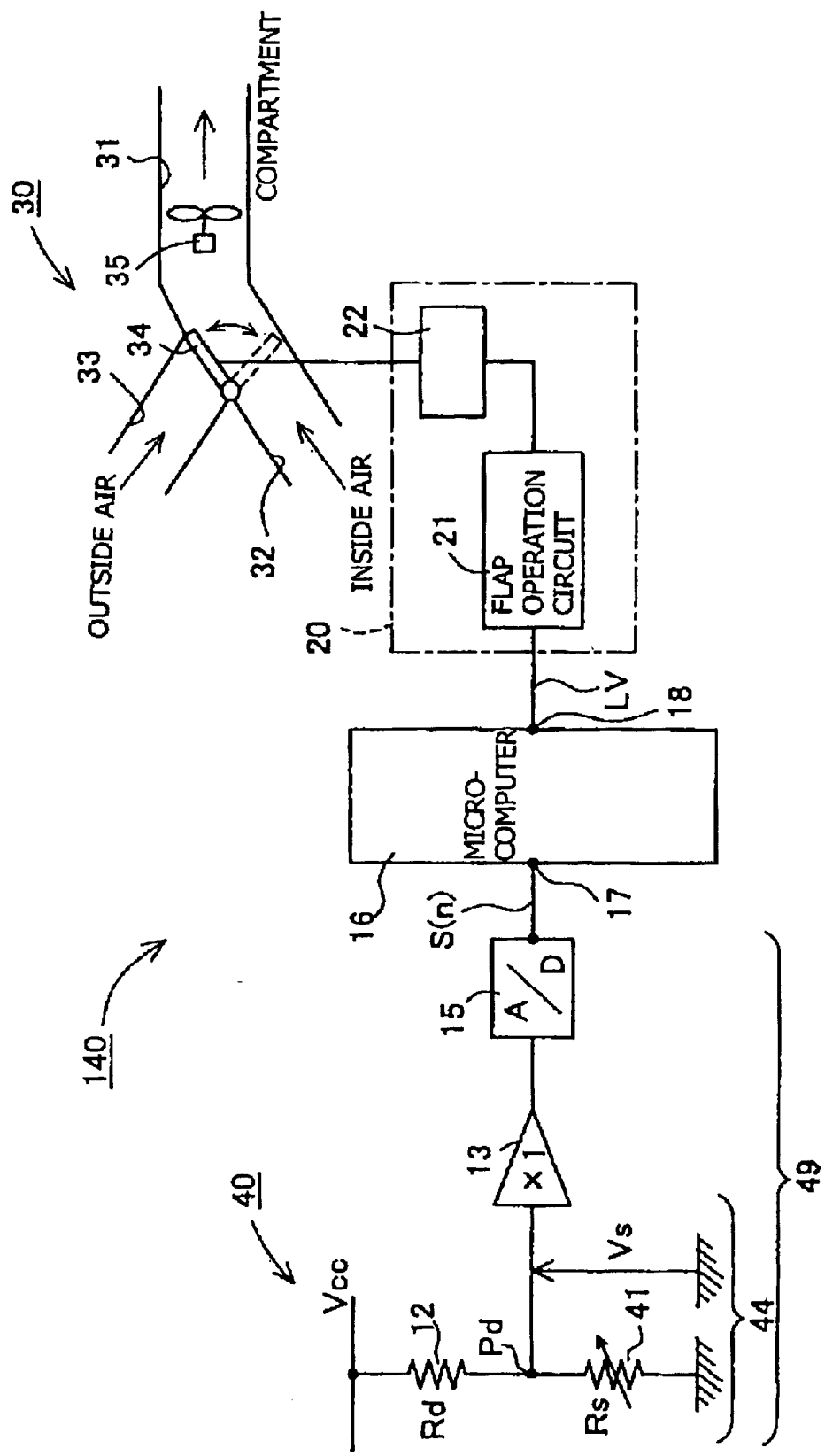
FIG. 6 is an explanatory view for schematically showing the gas detection apparatus and the vehicle automatic ventilation system according to the second embodiment of the invention.

In the aforementioned embodiments, the gas sensor element 11 or 41 is positioned on the ground side (lower side) of the voltage division circuit, and the detection resistor 12 is positioned on the power supply side (upper side) of the circuit (see FIG. 1 or 6). However, the positions of the gas sensor element 11 or 41 and the detection resistor 12 may be reversed such that the gas sensor element 11 or 41 is positioned on the power supply side (upper side) of the voltage division circuit, and the detection resistor 12 is positioned on the ground side (lower side) of the circuit. In this case, the sensor resistance conversion circuit has a reversed characteristic; i.e., the sensor voltage Vs decreases when the concentration of $NO_x$ increases. Therefore, processing for such a reversed characteristic is required.

A sensor output acquisition circuit having a structure different from that of the aforementioned sensor output acquisition circuit may be employed. For example, a circuit disclosed in Japanese Patent Application Laid-Open (kokai) No. 2001-242113 may be employed.

In the aforementioned embodiments and modifications, the base value B(n) (i.e., the first calculated value) is calculated from the sensor output value S(n) by use of Expression (1) or (5). However, the first calculated value may be calculated by means of another calculation method. Expression (1) includes, as the reference term, the tracking term for providing a value which follows the sensor output value and which changes more slowly than does the sensor output value; specifically the term B(n−1)+k1[S(n)−B(n−1)]. However, no particular limitations are imposed on the reference term, so long as it provides a value which follows the sensor output value and which changes more slowly than does the sensor output value. Examples of the reference term which may be employed include a term for providing a moving average value (e.g., {S(n)+S(n−1)+ . . . S(n−m)}/m) and a term for providing an integral value. The reference term may be an increasing term for providing a value which, regardless of the sensor output value, increases from a predetermined value with passage of time (e.g., E+k.n (wherein E denotes a constant and k denotes a coefficient) as disclosed in Japanese Patent Application Laid-Open (kokai) No. 1-199142). Alternatively, the reference term may be a combination of a tracking term and an increasing term.

Expression (1) includes the term −k2[S(n)−S(n−q)] (wherein q=5) as the increase-emphasizing term. However, the increase-emphasizing term may be a term for providing the difference between a present sensor output value S(n) and a $q^{th}$ past sensor output value S(n−q), such as a term −k[S(n)−S(n−1)] (wherein k denotes a coefficient) for providing the difference between a present sensor output value S(n) and the preceding sensor output value S(n−1). The number of cycles q, r, t, or u employed in the embodiments may be determined in consideration of responsiveness of a gas sensor element to be employed, cycle interval (sampling period), humidity, temperature, and other disturbances, as well as the shortest period of variation of a sensor output value attributed to such disturbance. In the aforementioned embodiments and modifications, q, r, t, and u are set to 5. However, q may differ from r, and t may differ from u. Preferably, q equals to r, and t equals to u. When q equals to r, or t equals to u, before and after switching of a concentration signal, the sensor output value in the same cycle can be used for calculating a base. Therefore, a continuously varying sensor output value can be employed.

The increase-emphasizing term may be a term employing merely the sensor output value, such as −k[E−S(n)] (wherein k denotes a coefficient and E denotes a constant), in consideration of the relation between the increase-emphasizing term and the reference term.

Expression (5) includes, as the reference term, the tracking term B(n−1)+k5[S(n)−B(n−1)]. However, the reference term may be a decreasing term for providing a value which decreases from a predetermined value with passage of time (e.g., E−k.n (wherein E denotes a constant and k denotes a coefficient)). Expression (5) includes the term −k6[S(n)−S(n−5)] as the decrease-emphasizing term. However, the decrease-emphasizing term may be a term such as −k[S(n)−S(n−r)] (wherein k denotes a coefficient and r denotes a positive integer). The decrease-emphasizing term may be a term employing merely the sensor output value, such as −k[E−S(n)] (wherein k denotes a coefficient and E denotes a constant), in consideration of the relation between the decrease-emphasizing term and the reference term. Therefore, in order to provide the first calculated value C1(n), for example, the following expression: C1(n)={S(n)+S(n−1)+ . . . S(n−m)}/m−k[E−S(n)] may be employed.

The base value B(n) (i.e., the second calculated value) is calculated from the sensor output value S(n) by use of Expression (4) or (8). However, as in the case of the first calculated value, the second calculated value may be calculated by means of another calculation method. Each of the second tracking term, second increase-emphasizing term, and second decrease-emphasizing term may be a term other than that described above in the embodiments. Therefore, in order to provide the second calculated value C2(n), for example, the following expression: C2(n)={S(n)+S(n−1)+ . . . S(n−m)}/m−k[E−S(n)] may be employed.

In the aforementioned embodiments and modifications, the base value B(n) calculated by use of Expression (1) or (5) is employed as the first calculated value, and the base value B(n) calculated by use of Expression (4) or (8) is employed as the second calculated value. However, the expression which is used for calculating the second calculated value during periods in which the high-concentration signal is being generated is not required to be the same as that used for calculating the second calculated value during periods in which the low-concentration signal is being generated. Therefore, a first order derivative or a second order derivative may be employed as the second calculated value.

In the aforementioned embodiments and modifications, the difference value D(n) is calculated from the sensor output value S(n) and the base value B(n) by use of Expression (2) or (6), and switching of the concentration signal is determined on the basis of the results of comparison between the difference value D(n) and the high-concentration threshold Tu or the low-concentration threshold Td. However, switching of the concentration signal may be determined on the basis of the results of determination as to satisfaction of other relations, for example, the results of comparison between the threshold and the ratio between the sensor output value and the base value.

In the aforementioned first and second embodiments, in steps S14 and S214, the sensor output value S(n) is compared with the preceding base value B(n−1). However, the sensor output value S(n) may be compared with the base value B(n−m): i.e., the base value obtained m cycle intervals before the present. For example, the sensor output value S(n) may be compared with the base value obtained 2 cycle intervals before the present (i.e., B(n−2)) or the base value obtained 3 cycle intervals before the present (i.e., B(n−3)). However, when the number of cycles m is set to 2 or more, in some periods, the relation in magnitude between the base value B(n−1), B(n−2), etc. and the corresponding sensor output value S(n−1), S(n−2), etc. may be reversed. In such a case, when the gas concentration increases, difficulty may be encountered in detecting an increase in the gas concentration. Therefore, preferably, m is set to 1 as describe above in the first and second embodiments.

In the aforementioned embodiments and modifications, the microcomputer 16 outputs the concentration signal LV of high level (i.e., high-concentration signal) and the concentration signal LV of low level (i.e., low-concentration signal). However, the microcomputer 16 may output a high-concentration signal which assumes any one of a plurality of signal levels and a low-concentration signal which assumes any one of a plurality of signal levels. Even in this case, the present invention can be applied to switching between the signal level corresponding to the high-concentration signal and the signal level corresponding to the low-concentration signal.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A gas detection apparatus using a gas sensor element whose electrical characteristics change in accordance with concentration of a specific gas, comprising:

acquisition means for acquiring a sensor output value at predetermined cycle intervals by use of the gas sensor element, the sensor output value increasing with concentration of the specific gas;

first calculation means for calculating a present first calculated value at the predetermined cycle intervals during a period in which a low-concentration signal is being generated, the present first calculated value representing a first calculated value at the present time and being calculated by use of a first calculation expression on the basis of a present sensor output value representing a sensor output value at the present time;

the first calculation expression including:

a reference term including at least one of a tracking term which, while tracking the sensor output value, changes more slowly than does the sensor output value, and an increasing term which gradually increases irrespective of changes in the sensor output value, and an increase-emphasizing term using the present sensor output value and determined in such a manner that the present first calculated value calculated for a time series of sensor output values that are increasing monotonously becomes smaller than a virtual present first calculated value for the time series by use of a virtual first calculation expression obtained through omission of the increase-emphasizing term, and the present first calculated value decreases with the rate of increase in the sensor output values of the time series; and high-concentration-signal generation means for generating a high-concentration signal in place of the low-concentration signal when the present sensor output value and the present first calculated value satisfy a predetermined first relation during the period in which the low-concentration signal is being generated.

2. A gas detection apparatus using a gas sensor element whose electrical characteristics change in accordance with concentration of a specific gas, comprising:

acquisition means for acquiring a sensor output value at predetermined cycle intervals by use of the gas sensor element, the sensor output value increasing with concentration of the specific gas;

first calculation means for calculating a present first calculated value at the predetermined cycle intervals during a period in which a low-concentration signal is being generated, the present first calculated value representing a first calculated value at the present time, wherein when a present sensor output value representing a sensor output value at the present time is greater than an $m^{th}$ past first calculated value representing the first calculated value calculated in a past cycle preceding the present cycle by m cycles, the first calculation means calculates the present first calculated value by use of a first calculation expression on the basis of the present sensor output value, the first calculation expression includes:

a reference term including at least one of a tracking term which, while tracking the sensor output value, changes more slowly than does the sensor output value, and an increasing term which gradually increases irrespective of changes in the sensor output value, and an increase-emphasizing term using the present sensor output value and determined in such a manner that the present first calculated value, calculated for a time series of sensor output values having an increase period in which the sensor output values increase monotonously and a decrease period subsequent to the increase period and in which the sensor output values decrease monotonously, becomes smaller, in the increase period, than a virtual present first calculated value for the time series by use of a virtual first calculation expression obtained through omission of the increase-emphasizing term, the present first calculated value decreasing with the rate of increase in the sensor output values of the time series, and, during the decrease period, the present first calculated value changing at a rate greater than a rate of change of the virtual present first calculated value, and when the present sensor output value is smaller than the $m^{th}$ past first calculated value, the first calculation means employs the present sensor output value as the present first calculated value; and high-concentration-signal generation means for generating a high-concentration signal in place of the low-concentration signal when the present sensor output value and the present first calculated value satisfy a predetermined first relation during the period in which the low-concentration signal is being generated.

3. A gas detection apparatus using a gas sensor element whose electrical characteristics change in accordance with concentration of a specific gas, comprising:

acquisition means for acquiring a sensor output value at predetermined cycle intervals by use of the gas sensor element, the sensor output value decreasing as concentration of the specific gas increases;

first calculation means for calculating a present first calculated value at the predetermined cycle intervals during a period in which a low-concentration signal is being generated, the present first calculated value representing a first calculated value at the present time and being calculated by use of a first calculation expression on the basis of a present sensor output value representing a sensor output value at the present time;

the first calculation expression including:

a reference term including at least one of a tracking term which, while tracking the sensor output value, changes more slowly than does the sensor output value, and a decreasing term which gradually decreases irrespective of changes in the sensor output value, and a decrease-emphasizing term using the present sensor output value and determined in such a manner that the present first calculated value calculated for a time series of sensor output values that are decreasing monotonously becomes greater than a virtual present first calculated value for the time series by use of a virtual first calculation expression obtained through omission of the decrease-emphasizing term, and the present first calculated value increases with the rate of decrease in the sensor output values of the time series; and high-concentration-signal generation means for generating a high-concentration signal in place of the low-concentration signal when the present sensor output value and the present first calculated value satisfy a predetermined first relation during the period in which the low-concentration signal is being generated.

4. A gas detection apparatus using a gas sensor element whose electrical characteristics change in accordance with concentration of a specific gas, comprising:

acquisition means for acquiring a sensor output value at predetermined cycle intervals by use of the gas sensor element, the sensor output value decreasing as concentration of the specific gas increases;

first calculation means for calculating a present first calculated value at the predetermined cycle intervals during a period in which a low-concentration signal is being generated, the present first calculated value representing a first calculated value at the present time, wherein when a present sensor output value representing a sensor output value at the present time is smaller than an $m^{th}$ past first calculated value representing the first calculated value calculated in a past cycle preceding the present cycle by m cycles, the first calculation means calculates the present first calculated value by use of a first calculation expression on the basis of the present sensor output value, the first calculation expression includes a reference term including at least one of a tracking term which, while tracking the sensor output value, changes more slowly than does the sensor output value, and a decreasing term which gradually decreases irrespective of changes in the sensor output value, and a decrease-emphasizing term using the present sensor output value and determined in such a manner that the present first calculated value, calculated for a time series of sensor output values having a decrease period in which the sensor output values decrease monotonously and an increase period subsequent to the decrease period and in which the sensor output values increase monotonously, becomes greater, in the decrease period, than a virtual present first calculated value for the time series by use of a virtual first calculation expression obtained through omission of the decrease-emphasizing term, the present first calculated value increasing with the rate of decrease in the sensor output values of the time series, and, during the increase period, the present first calculated value changing at a rate smaller than a rate of change of the virtual present first calculated value, and when the present sensor output value is greater than the $m^{th}$ past first calculated value, the first calculation means employs the present sensor output value as the present first calculated value; and high-concentration-signal generation means for generating a high-concentration signal in place of the low-concentration signal when the present sensor output value and the present first calculated value satisfy a predetermined first relation during the period in which the low-concentration signal is being generated.

5. A gas detection apparatus according to claim 2, wherein the $m^{th}$ past first calculated value is preferably a preceding first calculated value calculated in a preceding cycle.

6. A gas detection apparatus according to claim 4, wherein the $m^{th}$ past first calculated value is preferably a preceding first calculated value calculated in a preceding cycle.

7. A gas detection apparatus according to claim 1, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated.

8. A gas detection apparatus according to claim 2, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated.

9. A gas detection apparatus according to claim 3, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated.

10. A gas detection apparatus according to claim 4, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated.

11. A gas detection apparatus according to claim 5, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated.

12. A gas detection apparatus according to claim 6, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time; and low-concentration-signal generation means for generating the low-concentration signal in place of the high-concentration signal when the present second calculated value satisfies a predetermined second relation in the period in which the high-concentration signal is being generated.

13. A gas detection apparatus according to claim 1, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time, and the second calculation means calculating the present second calculated value by use of a second calculation expression including a second reference term including at least one of a second tracking term which, while tracking the sensor output value, changes more slowly than does the sensor output value, and a second increasing term which gradually increases irrespective of changes in the sensor output value, and a second increase-emphasizing term using the present sensor output value and determined in such a manner that the present second calculated value calculated for a time series of sensor output values having an increase period in which the sensor output values increase monotonously and a decrease period which is subsequent to the increase period and in which the sensor output values decrease monotonously, becomes smaller, in the increase period, than a virtual present second calculated value for the time series by use of a virtual second calculation expression obtained through omission of the second increase-emphasizing term, the present second calculated value decreasing with the rate of increase in the sensor output values of the time series, and, during the decrease period, the present second calculated value changing at a rate greater than a rate of change of the virtual present second calculated value; and low-concentration-signal generation means for generating the low-concentration signal in place of the high-concentration signal when the present sensor output value and the present second calculated value satisfy a predetermined second relation during the period in which the high-concentration signal is being generated.

14. A gas detection apparatus according to claim 2, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time, and the second calculation means calculating the present second calculated value by use of a second calculation expression including a second reference term including at least one of a second tracking term which, while tracking the sensor output value, changes more slowly than does the sensor output value, and a second increasing term which gradually increases irrespective of changes in the sensor output value, and a second increase-emphasizing term using the present sensor output value and determined in such a manner that the present second calculated value calculated for a time series of sensor output values having an increase period in which the sensor output values increase monotonously and a decrease period which is subsequent to the increase period and in which the sensor output values decrease monotonously, becomes smaller, in the increase period, than a virtual present second calculated value for the time series by use of a virtual second calculation expression obtained through omission of the second increase-emphasizing term, the present second calculated value decreasing with the rate of increase in the sensor output values of the time series, and, during the decrease period, the present second calculated value changing at a rate greater than a rate of change of the virtual present second calculated value; and low-concentration-signal generation means for generating the low-concentration signal in place of the high-concentration signal when the present sensor output value and the present second calculated value satisfy a predetermined second relation during the period in which the high-concentration signal is being generated.

15. A gas detection apparatus according to claim 3, comprising:

second calculation means for calculating a present second calculated value by use of the present sensor output value at the predetermined cycle intervals during a period in which the high-concentration-signal generation means is generating the high-concentration signal, the present second calculated value representing a second calculated value at the present time, and the second calculation means calculating the present second calculated value by use of a second calculation expression including a second reference term including at least one of a second tracking term which, while tracking the sensor output value, changes more slowly than does the sensor output value, and a second decreasing term which gradually decreases irrespective of changes in the sensor output value, and a second decrease-emphasizing term using the present sensor output value and determined in such a manner that the present second calculated value calculated for a time series of sensor output values having a decrease period in which the sensor output values decrease monotonously and an increase period which is subsequent to the decrease period and in which the sensor output values increase monotonously, becomes greater, in the decrease period, than a virtual present second calculated value for the time series by use of a virtual second calculation expression obtained through omission of the second decrease-emphasizing term, the present second calculated value increasing with the rate of decrease in the sensor output values of the time series, and, during the increase period, the present second calculated value changing at a rate smaller than a rate of change of the virtual present second calculated value; and low-concentration-signal generation means for generating the low-concentration signal in place of the high-concentration signal when the present sensor output value and the present second calculated value satisfy a predetermined second relation during the period in which the high-concentration signal is being generated.

16. A gas detection apparatus according to claim 4, comprising:
second calculation means for calculating a present second calculated value by use of the present sensor output value at the predetermined cycle intervals during a period in which the high-concentration-signal generation means is generating the high-concentration signal, the present second calculated value representing a second calculated value at the present time, and the second calculation means calculating the present second calculated value by use of a second calculation expression including
a second reference term including at least one of a second tracking term which, while tracking the sensor output value, changes more slowly than does the sensor output value, and a second decreasing term which gradually decreases irrespective of changes in the sensor output value, and
a second decrease-emphasizing term using the present sensor output value and determined in such a manner that the present second calculated value calculated for a time series of sensor output values having a decrease period in which the sensor output values decrease monotonously and an increase period which is subsequent to the decrease period and in which the sensor output values increase monotonously, becomes greater, in the decrease period, than a virtual present second calculated value for the time series by use of a virtual second calculation expression obtained through omission of the second decrease-emphasizing term, the present second calculated value increasing with the rate of decrease in the sensor output values of the time series, and, during the increase period, the present second calculated value changing at a rate smaller than a rate of change of the virtual present second calculated value; and
low-concentration-signal generation means for generating the low-concentration signal in place of the high-concentration signal when the present sensor output value and the present second calculated value satisfy a predetermined second relation during the period in which the high-concentration signal is being generated.

17. A gas detection apparatus using a gas sensor element whose electrical characteristics change in accordance with concentration of a specific gas, comprising:
acquisition means for acquiring a sensor output value S(n) at predetermined cycle intervals by use of the gas sensor element, the sensor output value S(n) increasing with concentration of the specific gas, where n is an integer representing the chronological order of each sensor output value in a time series of sensor output values;
first base-value calculation means for calculating a base value B(n) at the predetermined cycle intervals during a period in which a low-concentration signal is being generated, the base value B(n) being calculated in accordance with Expression (1):

$$B(n)=B(n-1)+k1[S(n)-B(n-1)]-k2[S(n)-S(n-q)] \tag{1}$$

where k1 and k2 are first and second coefficients, 0<k1<1, K2>0, and q is a positive integer;

differential-value calculation means for calculating a difference value D(n) in accordance with Expression (2):

$$D(n)=S(n)-B(n) \tag{2}$$

on the basis of the sensor output value S(n) and the base value B(n); and
high-concentration-signal generation means for generating a high-concentration signal when the difference value D(n) is greater than a high-concentration threshold Tu.

18. A gas detection apparatus using a gas sensor element whose electrical characteristics change in accordance with concentration of a specific gas, comprising:
acquisition means for acquiring a sensor output value S(n) at predetermined cycle intervals by use of the gas sensor element, the sensor output value S(n) increasing with concentration of the specific gas, where n is an integer representing the chronological order of each sensor output value in a time series of sensor output values;
first base-value calculation means for calculating a base value B(n) at the predetermined cycle intervals during a period in which a low-concentration signal is being generated, wherein
when the sensor output value S(n) is greater than a preceding base value B(n−1) representing a base value calculated in a preceding cycle, the first base-value calculation means calculates the base value B(n) in accordance with Expression (1):

$$B(n)=B(n-1)+k1[S(n)-B(n-1)]-k2[S(n)-S(n-q)] \tag{1}$$

where k1 and k2 are first and second coefficients, 0<k1<1, K2>0, and q is a positive integer, and
when the sensor output value S(n) is smaller than the preceding base value B(n−1), the first base-value calculation means calculates the base value B(n) in accordance with Expression (3):

$$B(n)=S(n) \tag{3};$$

differential-value calculation means for calculating a difference value D(n) in accordance with Expression (2):

$$D(n)=S(n)-B(n) \tag{2}$$

on the basis of the sensor output value S(n) and the base value B(n); and
high-concentration-signal generation means for generating a high-concentration signal when the difference value D(n) is greater than a high-concentration threshold Tu.

19. A gas detection apparatus according to claim 17, comprising:
second base-value calculation means for calculating a base value B(n) in accordance with Expression (4) at the predetermined cycle intervals during a period in which the high-concentration signal is being generated:

$$B(n)=B(n-1)+k3[S(n)-B(n-1)]-k4[S(n)-S(n-r)] \tag{4}$$

where k3 and k4 are third and fourth coefficients, 0<k3<1, K4>0, and r is a positive integer; and
low-concentration-signal generation means for generating a low-concentration signal when the difference value D(n) is smaller than a low-concentration threshold Td.

20. A gas detection apparatus according to claim 18, comprising:

second base-value calculation means for calculating a base value B(n) in accordance with Expression (4) at the predetermined cycle intervals during a period in which the high-concentration signal is being generated:

$$B(n)=B(n-1)+k3[S(n)-B(n-1)]-k4[S(n)-S(n-r)] \quad (4)$$

where k3 and k4 are third and fourth coefficients, 0<k3<1, K4>0, and r is a positive integer; and low-concentration-signal generation means for generating a low-concentration signal when the difference value D(n) is smaller than a low-concentration threshold Td.

21. A gas detection apparatus using a gas sensor element whose electrical characteristics change in accordance with concentration of a specific gas, comprising:

acquisition means for acquiring a sensor output value S(n) at predetermined cycle intervals by use of the gas sensor element, the sensor output value S(n) decreasing as concentration of the specific gas increases, where n is an integer representing the chronological order of each sensor output value in a time series of sensor output values;

third base-value calculation means for calculating a base value B(n) at the predetermined cycle intervals during a period in which a low-concentration signal is being generated, the base value B(n) being calculated in accordance with Expression (5):

$$B(n)=B(n-1)+k5[S(n)-B(n-1)]-k6[S(n)-S(n-t)] \quad (5)$$

where k5 and k6 are fifth and sixth coefficients, 0<k5<1, K6>0, and t is a positive integer;

differential-value calculation means for calculating a difference value D(n) in accordance with Expression (6):

$$D(n)=B(n)-S(n) \quad (6)$$

on the basis of the sensor output value S(n) and the base value B(n); and high-concentration-signal generation means for generating a high-concentration signal when the difference value D(n) is greater than a high-concentration threshold Tu.

22. A gas detection apparatus using a gas sensor element whose electrical characteristics change in accordance with concentration of a specific gas, comprising:

acquisition means for acquiring a sensor output value S(n) at predetermined cycle intervals by use of the gas sensor element, the sensor output value S(n) decreasing as concentration of the specific gas increases, where n is an integer representing the chronological order of each sensor output value in a time series of sensor output values;

third base-value calculation means for calculating a base value B(n) at the predetermined cycle intervals during a period in which a low-concentration signal is being generated, wherein when the sensor output value S(n) is smaller than a preceding base value B(n-1) representing a base value calculated in a preceding cycle, the third base-value calculation means calculates the base value B(n) in accordance with Expression (5):

$$B(n)=B(n-1)+k5[S(n)-B(n-1)]-k6[S(n)-S(n-t)] \quad (5)$$

where k5 and k6 are fifth and sixth coefficients, 0<k5<1, K6>0, and t is a positive integer, and when the sensor output value S(n) is greater than the preceding base value B(n-1), the third base-value calculation means calculates the base value B(n) in accordance with Expression (7):

$$B(n)=S(n) \quad (7);$$

differential-value calculation means for calculating a difference value D(n) in accordance with Expression (6):

$$D(n)=B(n)-S(n) \quad (6)$$

on the basis of the sensor output value S(n) and the base value B(n); and high-concentration-signal generation means for generating a high-concentration signal when the difference value D(n) is greater than a high-concentration threshold Tu.

23. A gas detection apparatus according to claim 21, comprising:

fourth base-value calculation means for calculating a base value B(n) in accordance with Expression (8) at the predetermined cycle intervals during a period in which the high-concentration signal is being generated:

$$B(n)=B(n-1)+k7[S(n)-B(n-1)]-k8[S(n)-S(n-u)] \quad (8)$$

where k7 and k8 are seventh and eighth coefficients, 0<k7<1, K8>0, and u is a positive integer; and low-concentration-signal generation means for generating a low-concentration signal when the difference value D(n) is smaller than a low-concentration threshold Td.

24. A gas detection apparatus according to claim 22, comprising:

fourth base-value calculation means for calculating a base value B(n) in accordance with Expression (8) at the predetermined cycle intervals during a period in which the high-concentration signal is being generated:

$$B(n)=B(n-1)+k7[S(n)-B(n-1)]-k8[S(n)-S(n-u)] \quad (8)$$

where k7 and k8 are seventh and eighth coefficients, 0<k7<1, k8>0, and u is a positive integer; and low-concentration-signal generation means for generating a low-concentration signal when the difference value D(n) is smaller than a low-concentration threshold Td.

25. An automatic ventilation system for a vehicle, comprising a gas detection apparatus according to any one of claims 1 to 24.

* * * * *